US012780874B2

(12) United States Patent
Choi et al.

(10) Patent No.: US 12,780,874 B2
(45) Date of Patent: Nov. 3, 2026

(54) NLRP3 INFLAMMASOME INHIBITORY PEPTIDE FOR TREATMENT OF INFLAMMATORY DISEASES

(71) Applicant: AJOU UNIVERSITY INDUSTRY—ACADEMIC COOPERATION FOUNDATION, Suwon-si (KR)

(72) Inventors: Sangdun Choi, Suwon-si (KR); Bilal Ahmad Rather, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 545 days.

(21) Appl. No.: 18/279,772

(22) PCT Filed: Apr. 20, 2022

(86) PCT No.: PCT/KR2022/005662
§ 371 (c)(1),
(2) Date: Aug. 31, 2023

(87) PCT Pub. No.: WO2022/225330
PCT Pub. Date: Oct. 27, 2022

(65) Prior Publication Data

US 2024/0309045 A1 Sep. 19, 2024

(30) Foreign Application Priority Data

Apr. 20, 2021 (KR) ........................ 10-2021-0050985

(51) Int. Cl.

| | |
|---|---|
| ***A61K 38/26*** | (2006.01) |
| ***A61K 9/00*** | (2006.01) |
| ***A61K 9/20*** | (2006.01) |
| ***A61K 38/10*** | (2006.01) |
| ***A61P 29/00*** | (2006.01) |
| ***C07K 7/06*** | (2006.01) |
| ***C07K 7/08*** | (2006.01) |

(52) U.S. Cl.
CPC ................ *C07K 7/08* (2013.01); *A61P 29/00* (2018.01); *C07K 7/06* (2013.01); *C07K 2319/00* (2013.01)

(58) Field of Classification Search
CPC ........ C07K 7/08; C07K 7/06; C07K 2319/00; C07K 2319/10; C07K 2319/03; A61P 29/00; A61P 3/00; A61P 25/00; A61P 37/00; A61K 38/00; A23L 33/18; A23V 2002/00; A23V 2200/324; A23V 2200/3262; A23V 2200/328; A23V 2200/332
See application file for complete search history.

(56) References Cited

U.S. PATENT DOCUMENTS

| | | | | |
|---|---|---|---|---|
| 6,911,306 B1 * | 6/2005 | Vertino | C12Q 1/6886 536/23.1 |
| 6,953,691 B2 * | 10/2005 | Reed | C07K 14/4747 435/243 |
| 7,300,749 B2 | 11/2007 | Bertin et al. | |
| 7,745,391 B2 * | 6/2010 | Mintz | A61P 37/00 514/19.3 |
| 9,029,636 B2 * | 5/2015 | Wu | C07K 14/415 800/320.2 |

FOREIGN PATENT DOCUMENTS

| | | |
|---|---|---|
| KR | 10-2012-0128413 A | 11/2012 |
| KR | 10-2016-0147099 A | 12/2016 |
| KR | 10-2020-0011272 A | 2/2020 |
| KR | 10-2020-0013630 A | 2/2020 |
| KR | 10-2022-0066071 A | 5/2022 |

(Continued)

OTHER PUBLICATIONS

Brown et al., Unusual biology across a group comprising more than 15% of domain Bacteria. Nature 523, 208-211 (2015). https://doi.org/10.1038/nature14486 (Year: 2015).*

Van Gorp et al., "Familial Mediterranean fever mutations lift the obligatory requirement for microtubules in Pyrin inflammasome activation", Proc. Natl. Acad. Sci. U.S.A. 113 (50) 14384-14389, https://doi.org/10.1073/pnas.1613156113 (2016). (Year: 2016).*

Pal, A., Neo, K., Rajamani, L. et al. Inhibition of NLRP3 inflammasome activation by cell-permeable stapled peptides. Sci Rep 9, 4913 (2019). https://doi.org/10.1038/s41598-019-41211-3 (Year: 2019).*

Touro College. (Jul. 11, 2024). Ozempic and Wegovy: What you need to know. Touro College of Pharmacy Touro University. https://tcop.touro.edu/news/stories/ozempic-and-wegovy-what-you-need-to-know.php#:~:text=It%20seems%20everyone%20is%20taking,an%20increase%20in%20counterfeit%20products. (Year: 2024).*

(Continued)

*Primary Examiner* — Lianko G Garyu
*Assistant Examiner* — Daliyah M. Brown
(74) *Attorney, Agent, or Firm* — Sughrue Mion, PLLC

(57) ABSTRACT

An inflammasome activates caspase-1 for cytokine maturation and cell death, and thus induces host defense in cells. An NLRP3 inflammasome promotes the release of highly inflammatory cytokines IL-1β and IL-18 to induce gasdermin D-mediated pyroptosis (pyroptotic cell death), and thus is involved in inflammatory processes. Therefore, targeting an NLRP3 pathway and modulating relevant immune responses can be a promising strategy for designing drug candidates for inflammatory diseases. A rationally designed α2-helix-based peptide NIP3 inhibits the NLRP3 pathway. NIP3 has remarkably inhibited both the secretion of NLRP3-induced IL-1β and IL-18 and the expression of downstream proteins in lipopolysaccharide-primed nigericin-activated THP-1 cells. In addition, binding energy data suggests that NIP3 has a stronger affinity for $ASC^{PYD}$ than for $NLRP3^{PYD}$. Therefore, according to empirical and in silico results, NIP3 exclusively inhibits the NLRP3-ASC-caspase-1 pathway.

10 Claims, 17 Drawing Sheets

Specification includes a Sequence Listing.

(56) References Cited

FOREIGN PATENT DOCUMENTS

| | | | |
|---|---|---|---|
| WO | 2019/120527 | A1 | 6/2019 |
| WO | 2020/037119 | A1 | 2/2020 |

OTHER PUBLICATIONS

Korean Office Action dated May 30, 2024 in Application No. 10-2021-0050985.
Korean Office Action dated May 15, 2023 in Korean Application No. 10-2021-0050985.
Lu et al., "Unified Polymerization Mechanism for the Assembly of ASC-dependent Inflammasomes", Cell, 2014, vol. 156, No. 6, pp. 1193-1206 (Manuscript pp. 1-28) (28 pages total).
Muller et al., "modlAMP: Python for antimicrobial peptides", Bioinformatics, 2017 (3 pages total).
Baoum et al., "Calcium condensed cell penetrating peptide complexes offer highly efficient, low toxicity gene silencing", International Journal of Pharmaceutics, 2012, vol. 427, pp. 134-142 (9 pages total).
Choi et al., "Intranasal delivery of the cytoplasmic domain of CTLA-4 using a novel protein transduction domain prevents allergic inflammation", Nature Medicine, 2006, vol. 12, No. 5, pp. 574-579 (6 pages total).
Chu et al., "An updated view on the structure and function of PYRIN domains", Apoptosis, 2015, vol. 20, pp. 157-173 (17 pages total).
Chu et al., "Rational modification of oligoarginine for highly efficient siRNA delivery: structure-activity relationship and mechanism of intracellular trafficking of siRNA", Nanomedicine: Nanotechnology, Biology, and Medicine, 2014, pp. 1-35 (36 pages total).
Dennison et al., Interactions of cell penetrating peptide Tat with model membranes: A biophysical study, Biochemical and Biophysical Research Communications, 2007, vol. 363, pp. 178-182 (5 pages total).
Derossi et al., "The Third Helix of the Antennapedia Homeodomain Translocates through Biological Membranes", The Journal of Biological Chemistry, 1994, vol. 269, No. 14, pp. 10444-10450 (7 pages total).
Deshayes et al., "Delivery of proteins and nucleic acids using a non-covalent peptide-based strategy", Advanced Drug Delivery Reviews, 2008, vol. 60, pp. 537-547 (11 pages total).
Elliott et al., "Intercellular Trafficking and Protein Delivery by a Herpesvirus Structural Protein" Cell, 1997, vol. 88, pp. 223-233 (11 pages total).
Elmquist et al., "Structure-activity relationship study of the cell-penetrating peptide pVEC", Biochimica et Biophysica Acta, 2006, pp. 721-729 (9 pages total).
Goldberg et al., "Drivers of age-related inflammation and strategies for healthspan extension" Immunol Rev., 2015, vol. 265, No. 1, pp. 1-21 (21 pages total).
Bauernfeind et al., "Cutting Edge: NF-kB Activating Pattern Recognition and Cytokine Receptors License NLRP3 Inflammasome Activation by Regulating NLRP3 Expression", J Immunol, 2009, vol. 183, pp. 787-791 (6 pages total).
Futaki et al., "Arginine-rich peptides: An Abundant Source of Membrane-Permeable Peptides Having Potential as Carriers for Intracellular Protein Delivery", The Journal of Biological Chemistry, 2001, vol. 276, No. 8, pp. 5836-5840 (6 pages total).
Galdiero et al., "gH625: A milestone in understanding the many roles of membranotropic peptides", Biochimica et Biophysica Acta, 2015, vol. 1848, pp. 16-25 (10 pages total).
Guo et al., "Inflammasomes: Mechanism of Action, Role in Disease, and Therapeutics" Nat Med, 2015, vol. 21, No. 7, pp. 1-27 (27 pages total).
Zahid et al., "Pharmacological Inhibitors of the NLRP3 Inflammasome", Frontiers in Immunology, 2019, vol. 10, No. 2538, pp. 1-10 (10 pages total).
Wen et al., "A role for the NLRP3 inflammasome in metabolic diseases and did Warburg miss inflammation?", Nat Immunol., 2014, vol. 13, No. 4, pp. 1-14 (14 pages total).
Swanson et al., "The NLRP3 inflammasome: molecular activation and regulation to therapeutics", Nat Rev Immunol, 2019, vol. 19, No. 8, pp. 1-28 (28 pages total).
Lamkanfi et al., "Inflammasomes and Their Roles in Health and Disease", Annu. Rev. Cell Dev. Biol. 2012, 16:24 (25 pages total).
Lamkanfi et al., "Mechanisms and Functions of Inflammasomes" Cell, 2014, vol. 157, pp. 1013-1022 (10 pages total).
Kelley et al., "The NLRP3 Inflammasome: An Overview of Mechanisms of Activation and Regulation", International Journal of Molecular Sciences, 2019, vol. 20, No. 3328, pp. 1-24 (24 pages total).
Oroz et al., "ASC PYRIN Domain Self-Associates and Binds NLRP3 Using Equivalent Binding Interfaces" J Biol. Chem. 2016, pp. 1-34 (34 pages total).
Pae et al., "Translocation of cell-penetrating peptides across the plasma membrane is controlled by cholesterol and microenvironment created by membranous proteins" Journal of Controlled Release, 2014, vol. 192, pp. 103-113 (11 pages total).
Pal et al., "Inhibition of NLRP3 inflammasome activation by cell-permeable stapled peptides", Scientific Reports, 2019, vol. 9, No. 4913, pp. 1-15 (15 pages total).
Duewell et al., "NLRP3 inflamasomes are required for atherogenesis and activated by cholesterol crystals that form early in disease", Nature, 2010, vol. 464, No. 7293, pp. 1-14 (14 pages total).
Grant et al., "Mechanisms of disease: inflammasome activation and the development of type 2 diabetes", Frontiers in Immunology, 2013, vol. 4, No. 50, pp. 1-10 (10 pages total).
Christgen et al., "Toward targeting inflammasomes: insights into their regulation and activation", Cell Research, 2020, vol. 30, pp. 315-327 (13 pages total).
Voet et al., "Inflammasomes in neuroinflammatory and neurodegenerative diseases", EMBO Molecular Medicine, 2019, vol. 11, pp. 1-16 (16 pages total).
Simeoni et al., "Insight into the mechanism of the peptide-based gene delivery system MPG: implications for delivery of siRNA into mammalian cells", Nucleic Acids Research, 2003, vol. 31, No. 11, pp. 2717-2724 (8 pages total).
Strowig et al., "Inflammasomes in health and disease", Nature, 2012, vol. 481, pp. 278-286 (9 pages total).
Srimathi et al., "Mapping of POP1-binding Site on Pyrin Domain of ASC", The Journal of Biological Chemistry, 2008, vol. 283, No. 22, pp. 15390-15398 (9 pages total).
Takeshima et al., "Membrane Transport Structure Function and Biogenesis: Translocation of Analogues of the Antimicrobial Peptides Magainin and Buforin across Human Cell Membranes", The Journal of Biological Chemistry, 2003, vol. 278, No. 2, pp. 1310-1315 (7 pages total).
Vanhee et al., "Protein-Peptide Interactions Adopt the Same Structural Motifs as Monomeric Protein Folds", Structure 17, 2009, pp. 1128-1136 (9 pages total).
You et al., "Potential Mean Force from Umbrella Sampling Simulations: What Can We Learn and What Is Missed?", J Chem Theory Comput, 2019, vol. 15, No. 4, pp. 2433-2443 (pp. 1-31) (31 pages total).
Wada et al., "Effect of Ala replacement with Aib in amphipathic cell-penetrating peptide on oligonucleotide delivery into cells", Bioorganic & Medicinal Chemistry, 2013, vol. 21, pp. 7669-7673 (5 pages total).
Wang et al., "Targeting NLRP3 (Nucleotide-Binding Domain, Leucine-Rich-Containing Family, Pyrin Domain—Containing-3) Inflammasome in Cardiovascular Disorders", Arterioscler Thromb Vasc Biol, 2018, vol. 38, pp. 2765-2779 (15 pages total).
Zhang et al., "C1q/TNF-related protein-9 attenuates atherosclerosis through AMPK-NLRP3 inflammasome singling pathway", International Immunopharmacology, 2019, pp. 1-5 (5 pages total).

* cited by examiner

NIP1: CPP-EELKKFKLKLLSV (SEQ ID NO: 1)
NIP2: CPP-RALKKAKIKLESV (SEQ ID NO: 2)
NIP3: CPP-RLARKAKQRLESV (SEQ ID NO: 3)

SEQUENCE LISTING

<160> NUMBER OF SEQ ID NOS: 21

<210> SEQ ID NO 1
<211> LENGTH: 13
<212> TYPE: PRT
<213> ORGANISM: Artificial Sequence
<220> FEATURE:
<223> OTHER INFORMATION: NLRP3/ASC-inhibitory peptide 1 (NIP1)

<400> SEQUENCE: 1

Glu Glu Leu Lys Lys Phe Lys Leu Lys Leu Leu Ser Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: NLRP3/ASC-inhibitory peptide 2 (NIP2)

<400> SEQUENCE: 2

Arg Ala Leu Lys Lys Ala Lys Ile Lys Leu Glu Ser Val
1 5 10

<210> SEQ ID NO 3
<211> LENGTH: 13
<212> TYPE: PRT
<213> ORGANISM: Artificial Sequence
<220> FEATURE:
<223> OTHER INFORMATION: NLRP3/ASC-inhibitory peptide 3 (NIP3)

<400> SEQUENCE: 3

Arg Leu Ala Arg Lys Ala Lys Gln Arg Leu Glu Ser Val
1 5 10

<210> SEQ ID NO 4
<211> LENGTH: 13
<212> TYPE: PRT
<213> ORGANISM: Artificial Sequence
<220> FEATURE:
<223> OTHER INFORMATION: NLRP3/ASC-inhibitory peptide 4 (NIP4)

<400> SEQUENCE: 4

Asp Val Asp Leu Lys Lys Phe Lys Met His Leu Glu Asp
1 5 10

<210> SEQ ID NO 5
<211> LENGTH: 13
<212> TYPE: PRT
<213> ORGANISM: Artificial Sequence
<220> FEATURE:
<223> OTHER INFORMATION: NLRP3/ASC-inhibitory peptide 5 (NIP5)

<400> SEQUENCE: 5

Ala His Asp Leu Lys Lys Val Lys Met Asp Leu Glu Asp
1 5 10

<210> SEQ ID NO 6
<211> LENGTH: 10
<212> TYPE: PRT
<213> ORGANISM: Artificial Sequence
<220> FEATURE:
<223> OTHER INFORMATION: NLRP3/ASC-inhibitory peptide 6 (NIP6)

<400> SEQUENCE: 6

Met Gly Arg Ala Arg Asp Ala Ile Leu Asp
1 5 10

<210> SEQ ID NO 7
<211> LENGTH: 11
<212> TYPE: PRT
<213> ORGANISM: Artificial Sequence
<220> FEATURE:
<223> OTHER INFORMATION: NLRP3/ASC-inhibitory peptide 7 (NIP7)

<400> SEQUENCE: 7

Asp Ala Leu Asp Leu Thr Asp Lys Leu Val Ser
1 5 10

<210> SEQ ID NO 8
<211> LENGTH: 11
<212> TYPE: PRT
<213> ORGANISM: Artificial Sequence
<220> FEATURE:

```
<223> OTHER INFORMATION: TAT peptide

<400> SEQUENCE: 8

Tyr Gly Arg Lys Lys Arg Arg Gln Arg Arg Arg
1               5                   10


<210> SEQ ID NO 9
<211> LENGTH: 13
<212> TYPE: PRT
<213> ORGANISM: Artificial Sequence
<220> FEATURE:
<223> OTHER INFORMATION: TAT(48-60)

<400> SEQUENCE: 9

Gly Arg Lys Lys Arg Arg Gln Arg Arg Arg Pro Pro Gln
1               5                   10


<210> SEQ ID NO 10
<211> LENGTH: 9
<212> TYPE: PRT
<213> ORGANISM: Artificial Sequence
<220> FEATURE:
<223> OTHER INFORMATION: TAT(49-57)

<400> SEQUENCE: 10

Arg Lys Lys Arg Arg Gln Arg Arg Arg
1               5


<210> SEQ ID NO 11
<211> LENGTH: 16
<212> TYPE: PRT
<213> ORGANISM: Artificial Sequence
<220> FEATURE:
<223> OTHER INFORMATION: Penetratin

<400> SEQUENCE: 11

Arg Gln Ile Lys Ile Trp Phe Gln Asn Arg Arg Met Lys Trp Lys Lys
1               5                   10                  15


<210> SEQ ID NO 12
<211> LENGTH: 8
<212> TYPE: PRT
<213> ORGANISM: Artificial Sequence
<220> FEATURE:
<223> OTHER INFORMATION: R8

<400> SEQUENCE: 12

Arg Arg Arg Arg Arg Arg Arg Arg
1               5


<210> SEQ ID NO 13
<211> LENGTH: 13
<212> TYPE: PRT
<213> ORGANISM: Artificial Sequence
<220> FEATURE:
<223> OTHER INFORMATION: R9-TAT

<400> SEQUENCE: 13

Gly Arg Arg Arg Arg Arg Arg Arg Arg Arg Pro Pro Gln
1               5                   10


<210> SEQ ID NO 14
<211> LENGTH: 21
<212> TYPE: PRT
<213> ORGANISM: Artificial Sequence
<220> FEATURE:
<223> OTHER INFORMATION: Pep-1
```

<400> SEQUENCE: 14

Lys Glu Thr Trp Trp Glu Thr Trp Trp Thr Glu Trp Ser Gln Pro Lys
1 5 10 15

Lys Lys Arg Lys Val
20

<210> SEQ ID NO 15
<211> LENGTH: 11
<212> TYPE: PRT
<213> ORGANISM: Artificial Sequence
<220> FEATURE:
<223> OTHER INFORMATION: Hph-1

<400> SEQUENCE: 15

Tyr Ala Arg Val Arg Arg Arg Gly Pro Arg Arg
1 5 10

<210> SEQ ID NO 16
<211> LENGTH: 18
<212> TYPE: PRT
<213> ORGANISM: Artificial Sequence
<220> FEATURE:
<223> OTHER INFORMATION: MAP

<400> SEQUENCE: 16

Lys Leu Ala Leu Lys Leu Ala Leu Lys Ala Leu Lys Ala Ala Leu Lys
1 5 10 15

Leu Ala

<210> SEQ ID NO 17
<211> LENGTH: 18
<212> TYPE: PRT
<213> ORGANISM: Artificial Sequence
<220> FEATURE:
<223> OTHER INFORMATION: pVEC

<400> SEQUENCE: 17

Leu Leu Ile Ile Leu Arg Arg Arg Ile Arg Lys Gln Ala His Ala His
1 5 10 15

Ser Lys

<210> SEQ ID NO 18
<211> LENGTH: 27
<212> TYPE: PRT
<213> ORGANISM: Artificial Sequence
<220> FEATURE:
<223> OTHER INFORMATION: MPG

<400> SEQUENCE: 18

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 19
<211> LENGTH: 27
<212> TYPE: PRT
<213> ORGANISM: Artificial Sequence
<220> FEATURE:
<223> OTHER INFORMATION: Transportan

<400> SEQUENCE: 19

Gly Trp Thr Leu Asn Ser Ala Gly Tyr Leu Leu Gly Lys Ile Asn Leu

-continued

```
1               5                   10                  15

Lys Ala Leu Ala Ala Leu Ala Lys Lys Ile Leu
            20                  25


<210> SEQ ID NO 20
<211> LENGTH: 20
<212> TYPE: PRT
<213> ORGANISM: Artificial Sequence
<220> FEATURE:
<223> OTHER INFORMATION: gH625

<400> SEQUENCE: 20

His Gly Leu Ala Ser Thr Leu Thr Arg Trp Ala His Tyr Asn Ala Leu
1               5                   10                  15

Ile Arg Ala Phe
            20


<210> SEQ ID NO 21
<211> LENGTH: 17
<212> TYPE: PRT
<213> ORGANISM: Artificial Sequence
<220> FEATURE:
<223> OTHER INFORMATION: VP22

<400> SEQUENCE: 21

Asn Ala Lys Thr Arg Arg His Glu Arg Arg Arg Lys Leu Ala Ile Glu
1               5                   10                  15

Arg
```

NLRP3 INFLAMMASOME INHIBITORY PEPTIDE FOR TREATMENT OF INFLAMMATORY DISEASES

CROSS REFERENCE TO RELATED APPLICATIONS

This application is a National Stage of International Application No. PCT/KR2022/005662 filed Apr. 20, 2022, claiming priority based on Korean Patent Application No. 10-2021-0050985 filed Apr. 20, 2021.

INCORPORATION BY REFERENCE OF SEQUENCE LISTING

The content of the electronically submitted sequence listing, file name: Q291119_SEQ_LIST_ST25.txt: size: 5,578 bytes; and date of creation: Aug. 25, 2023, filed herewith, is incorporated herein by reference in its entirety.

TECHNICAL FIELD

The present invention relates to peptides that inhibit NLRP3 inflammasome activity, and more particularly to an NLRP3-ASC interface-mimicking α2-helix-based peptide that inhibits NLRP3 inflammasome signaling by targeting $ASC^{PYD}$ and $NLRP3^{PYD}$, a fusion peptide in which the peptide and a cell-penetrating peptide (CPP) are conjugated, a composition for inhibiting NLRP3 inflammasome activity comprising the peptide or the fusion peptide, a composition for preventing or treating an NLRP3 inflammasome-related inflammatory disease, and a food composition for preventing or ameliorating an NLRP3 inflammasome-related inflammatory disease.

BACKGROUND ART

An inflammasome regulates the activation of caspase-1 and is a sensor and receptor of the innate immune system that induces inflammation in response to specific molecules derived from infectious microorganisms and host proteins (H. Guo, et al., *Nat. Med.* 21, 677-687 (2015)). Formation of an inflammasome supramolecular assembly depends on homotypic or heterotypic interactions between death domains to initiate, expand, and propagate pyroptosis signaling. Two death domains, including the pyrin domain (PYD) and the caspase activation and recruitment domain (CARD), form a filamentous complex, thus initiating inflammasome formation (L. H. Chu, et al., *Apoptosis* 20, 157-173 (2015)). The activated inflammasome recruits the bipartite PYD-CARD domain protein ASC (apoptosis-associated speck-like protein containing a CARD (caspase activation and recruitment domain), also known as PYCARD) through PYD-PYD interactions, and the CARD domain of ASC recruits the CARD domain of the caspase-1 inflammasome (M. Lamkanfi, V. M. Dixit, *Annu. Rev. Cell Dev. Biol.* 28, 137-161 (2012)). Proteins that make up the inflammasome assembly are potential therapeutic targets because aberrant signaling contributes to many infectious and autoimmune diseases (M. Lamkanfi, V. M. Dixit, *Cell* 157, 1013-1022 (2014); T. Strowig, et al., *Nature* 481, 278-286 (2012)). The NLRP3 inflammasome is the most extensively studied inflammasome and is involved in the activation by various stimuli and pathogenesis of various inflammation-related health problems, including diabetes, atherosclerosis, metabolic syndrome, cardiovascular diseases, and neurodegenerative diseases (N. Kelley, et al., *Int. J. Mol. Sci.* 20, 3328 (2019)).

Upon stimulation, NLRP3 (also known as NACHT, leucine-rich repeat, and pyrin domain (PYD)-containing protein 3 or NLR family pyrin domain containing 3) is oligomerized through homotypic interactions between NACHT domains (K. V. Swanson, et al., *Nat. Rev. Immunol.* 19, 477-489 (2019)). Oligomerized NLRP3 recruits ASCs through homotypic $NLRP3^{PYD}$ (PYD of NLRP3)-$ASC^{PYD}$ interactions and nucleates the formation of helical ASC filaments. This process is also mediated by the $ASC^{PYD}$-$ASC^{PYD}$ interaction. The adapter protein ASC connects the sensor protein and caspase-1 to form a three-membered inflammasome complex assembled through PYD interactions between the sensor and ASC and through CARD interactions between ASC and caspase-1. ASC self-associates and binds to $NLRP3^{PYD}$ through the corresponding protein region, with a higher binding affinity for the latter (J. Oroz, et al., *J. Biol. Chem.* 291, 19487-19501 (2016)). Based on these data, the present inventors analyzed the supramolecular complex interface formed by $ASC^{PYD}$ self-association and intermolecular $ASC^{PYD}$-$NLRP3^{PYD}$ oligomerization to thus provide a basis for NLRP3 inflammasome formation and regulation.

The general mechanism of NLRP3 activation leading to the formation of supramolecular assemblies has been determined by structural mutagenesis of homologous and heterologous PYD-PYD bonds (A. Lu, et al., *Cell* 156, 1193-1206 (2014)). NMR (nuclear magnetic resonance) spectroscopic and analytical ultracentrifugation-based characterization of $NLRP3^{PYD}$ and ASC self-association provides a deeper understanding of the molecular labyrinth mechanisms underlying intermolecular interactions. Structure-based mutations in $NLRP3^{PYD}$ abolish the nucleation ability of $ASC^{PYD}$, and mutations in $ASC^{PYD}$ disrupt the ability to form filaments. These observations highlight the importance of the PYD-PYD interaction in this pathway. While structural mutagenesis data highlight hotspots of the PYD interface, mimicking the interface with biologics may specifically target dysregulated inflammatory processes mediated by protein complexes containing PYD and CARD domains.

Accordingly, the present inventors have made great efforts to develop a new NLRP3 inflammasome inhibitor, and thus ascertained that an $ASC^{PYD}$-derived peptide, defined as NLRP3/ASC-inhibitory peptide 3 (NIP3), was identified as a potent NLRP3-specific inhibitor of interleukin (IL) 1β and IL-18 release ($IC_{50}$ (half-maximal inhibitory concentration) of 2-2.5 μM), and also that, based on results of Western blotting and analysis of toll-like receptor (TLR) 4 signaling of cross-mediated tumor necrosis factor (TNF)-α and cytokines IL-8 and TNF-α, NIP3 primarily targeted $NLRP3^{PYD}$, $ASC^{PYD}$, or both, and furthermore, based on results of analysis of NIP3-$ASC^{PYD}$ and NIP3-$NLRP3^{PYD}$ complexes by mimicking dissociation and association phenomena in umbrella sampling simulation similar to the experimental method for rough determination of binding affinity, NIP3 bound more strongly to $ASC^{PYD}$ than to $NLRP3^{PYD}$, thus culminating in the present invention.

The above information described in the background section is only for improving the understanding of the background of the present invention, and it does not include information forming the prior art known to those of ordinary skill in the art to which the present invention pertains.

SUMMARY OF THE INVENTION

It is an object of the present invention to provide a peptide having a function of inhibiting NLRP3 inflammasome activity.

It is another object of the present invention to provide a fusion peptide in which the peptide and a cell-penetrating peptide (CPP) are conjugated.

It is still another object of the present invention to provide a composition for inhibiting NLRP3 inflammasome activity comprising the peptide or the fusion peptide.

It is yet another object of the present invention to provide a composition for preventing or treating an NLRP3 inflammasome-related inflammatory disease comprising the peptide or the fusion peptide.

It is a further object of the present invention to provide a method of preventing or treating an NLRP3 inflammasome-related inflammatory disease using the peptide or the fusion peptide, the use of the peptide or the fusion peptide for the prevention or treatment of an NLRP3 inflammasome-related inflammatory disease, and the use of the peptide or the fusion peptide for the manufacture of a medicament for the prevention or treatment of an NLRP3 inflammasome-related inflammatory disease.

It is still a further object of the present invention to provide a food composition for preventing or ameliorating an NLRP3 inflammasome-related inflammatory disease comprising the peptide or the fusion peptide.

In order to accomplish the above objects, the present invention provides a peptide comprising any one amino acid sequence selected from the group consisting of SEQ ID NO: 1 to SEQ ID NO: 7.

In addition, the present invention provides a fusion peptide in which the peptide and a cell-penetrating peptide (CPP) are conjugated.

In addition, the present invention provides a composition for inhibiting NLRP3 inflammasome activity comprising the peptide or the fusion peptide.

In addition, the present invention provides a composition for preventing or treating an NLRP3 inflammasome-related inflammatory disease comprising the peptide or the fusion peptide.

In addition, the present invention provides a method of preventing or treating an NLRP3 inflammasome-related inflammatory disease comprising administering an effective amount of the peptide or the fusion peptide or a composition comprising the same.

In addition, the present invention provides the use of the peptide or the fusion peptide for the prevention or treatment of an NLRP3 inflammasome-related inflammatory disease.

In addition, the present invention provides the use of the peptide or the fusion peptide for the manufacture of a medicament for the prevention or treatment of an NLRP3 inflammasome-related inflammatory disease.

In addition, the present invention provides a food composition for preventing or ameliorating an NLRP3 inflammasome-related inflammatory disease comprising the peptide or the fusion peptide.

BRIEF DESCRIPTION OF DRAWINGS

FIG. 1A showing a model of NLRP3 inflammasome assembly, in which upon activation, the upstream sensor protein NLRP3 oligomerizes to form a platform for PYD that induces ASC filament assembly through PYD-PYD interactions, and $ASC^{PYD}$ self-associates and interacts with $NLRP3^{PYD}$ through the equivalent protein domain, FIGS. 1B and 1C showing computational design of NLRP3/ASC-inhibiting peptides (NIPs), using interacting helices of $NLRP3^{PYD}$ (FIG. 1B) and $ASC^{PYD}$ (FIG. 1C), FIG. 1D being a graph showing results of analysis of cell viability (MTT) after treatment of cells with the designed NIP at different concentrations, and FIG. 1E being a graph showing results of evaluation of the regulatory effect of peptides on the NLPR3 signaling pathway by ELISA, in which the data represent at least 4 independent experiments (n≥4) and bars represent mean±SD (*P<0.05, **P<0.01).

FIG. 4A being a graph showing $IC_{50}$ of NIP3, FIG. 4B being a graph showing the inhibitory effect of NIP3 on secreted IL-18 evaluated by ELISA, FIG. 4C showing the expression levels of NLPR3, pro-IL-1β, and caspase-1 quantified by Western blotting of total protein extracts from THP1-derived macrophages, with β serving as a loading control, FIG. 4D being a graph showing NLPR3-mediated secretion of IL-1β evaluated by ELISA, and FIGS. 4E and 4F being graphs showing the effect of NIP3 evaluated by ELISA, with the effect of NIP3 on TNFα-mediated IL-8 secretion (FIG. 4E) and LPS-mediated TNF-α secretion (FIG. 4F), in which the data represent at least 4 independent experiments and bars represent mean±SD (*P<0.05, **P<0.01).

DETAILED DESCRIPTION AND PREFERRED EMBODIMENTS OF THE INVENTION

Unless otherwise defined, all technical and scientific terms used herein have the same meanings as typically understood by those skilled in the art to which the present invention belongs. In general, the nomenclature used herein is well known in the art and is typical.

Dysregulation of NLRP3 inflammasome activation is a major causative factor in chronic inflammatory, metabolic, and neurodegenerative diseases and cancer. Pharmacological targeting of the inflammasome is being pursued as a strategy for the treatment of autoinflammatory diseases and cancer (S. Christgen, et al., *Cell Res.* 30, 315-327 (2020)). Multiple targets may be used for NLRP3 inhibition by exploiting a complex signaling cascade. Various tactics have been used to tackle the inflammasome for the development of NLRP3 inhibitors, but most are designed to block the ATP binding site. It is not easy to find drugs that selectively inhibit NLRP3 because the shrimp-like structure of NLRP3 does not have a clear binding pocket to which drugs may be attached. The currently available pool of blockers of NLRP3-NLRP3, NLRP3-ASC, ASC-ASC, or ASC-caspase-1 interactions is less developed (A. Zahid, et al., *Front Immunol.* 10, 2538 (2019)). Although targeting protein-protein interactions (PPIs) is difficult (H. Lu, et al., *Signal Transduct Target Ther.* 5, 213 (2020)), this approach may be advantageous as it may lead to better approaches and selective inhibition of NLRP3 inflammasome signaling. Therefore, rather than agonists or antagonists, signaling inhibitors (biological therapeutics) with high specificity and greater efficacy may be selected for drug development targeting NLRP3-NLRP3, NLRP3-ASC, or ASC-ASC PPI.

Figure 1A:
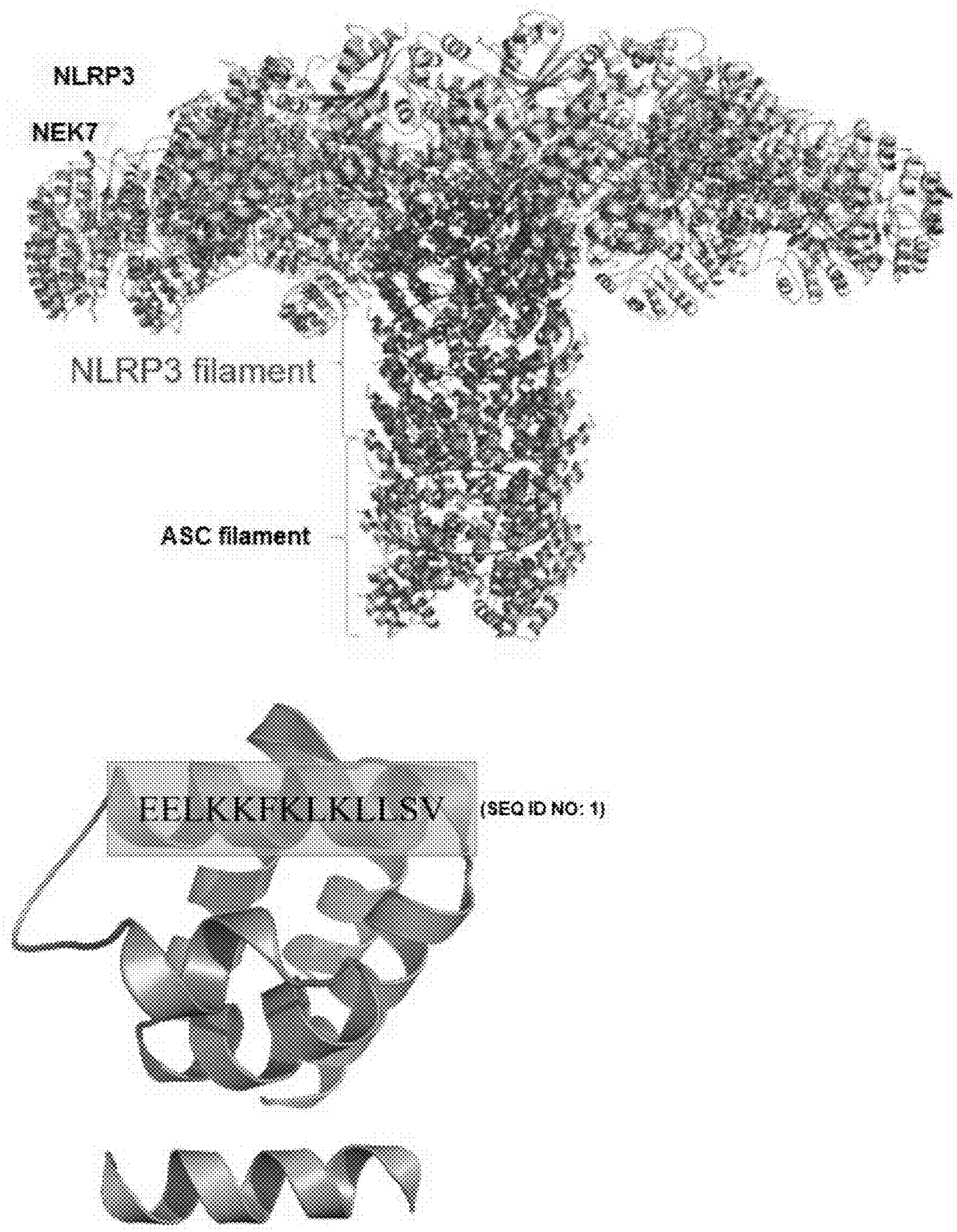
FIGS. 1A-1E show computational design and in vitro screening of peptides.
Figure 1B:
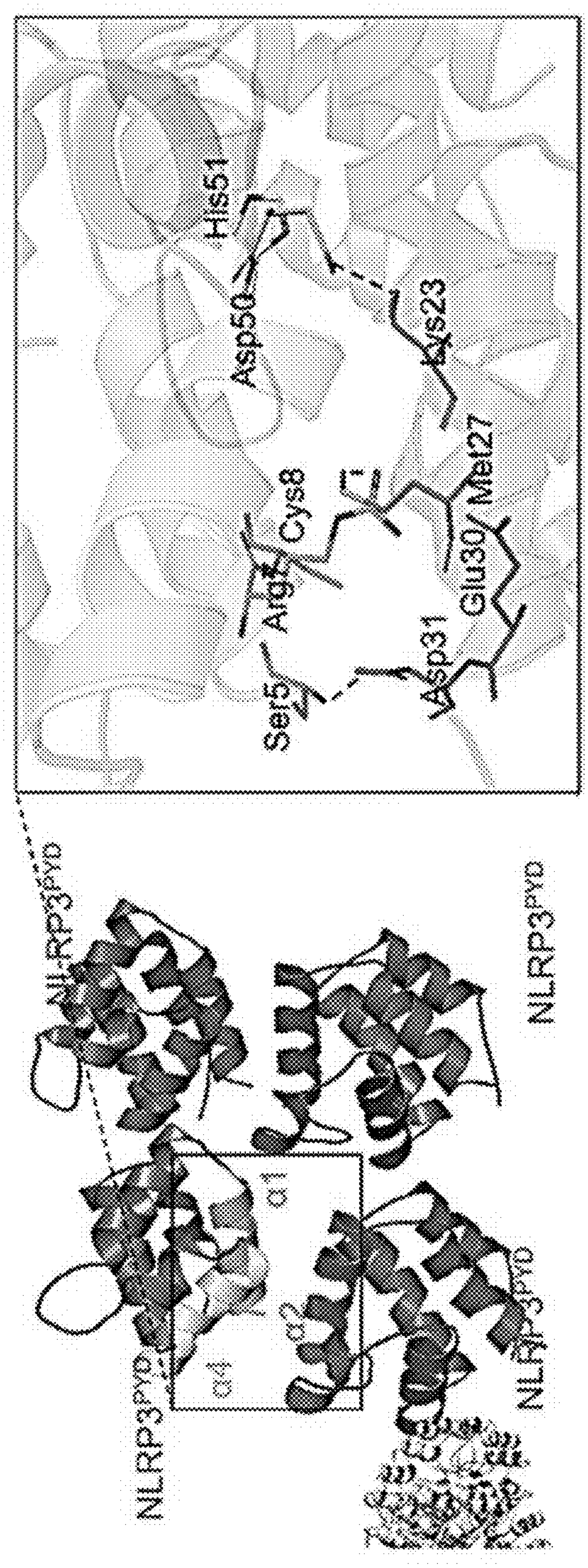
Figure 1C:
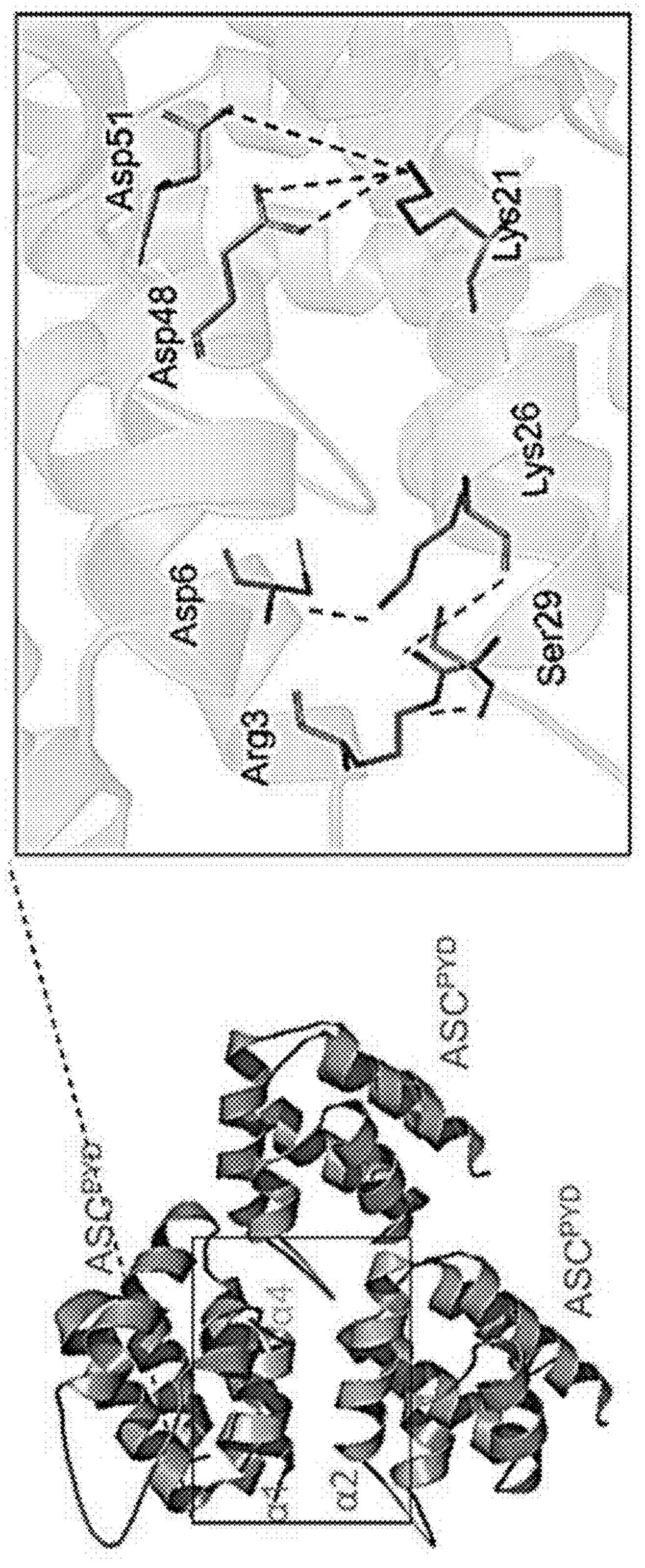
Figure 1D:
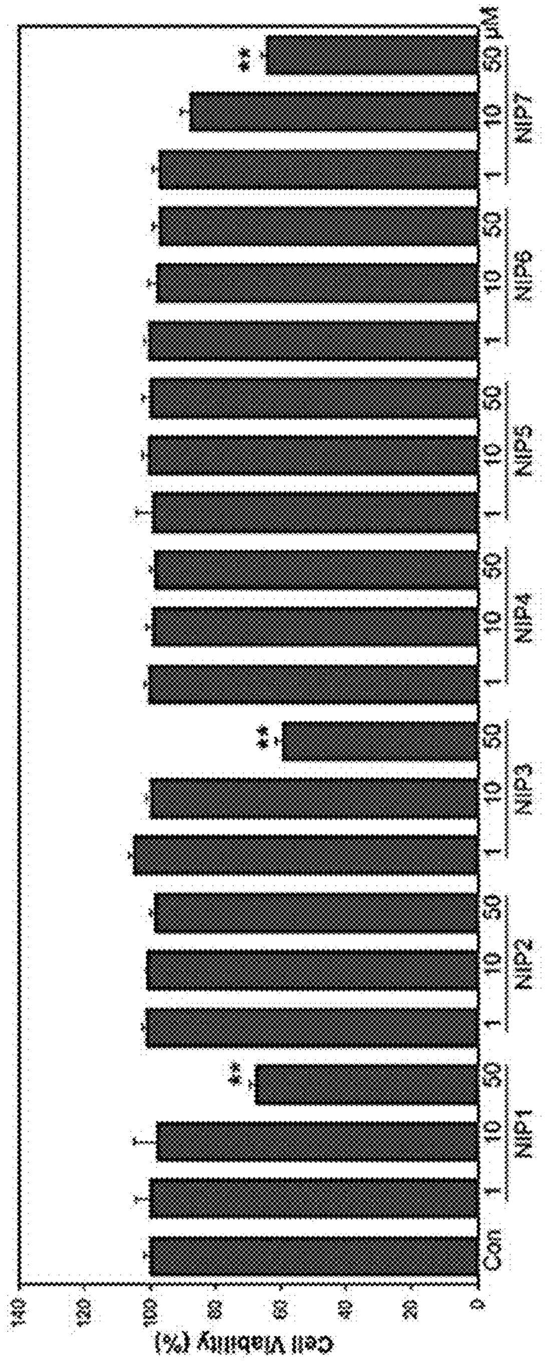
Figure 1E:
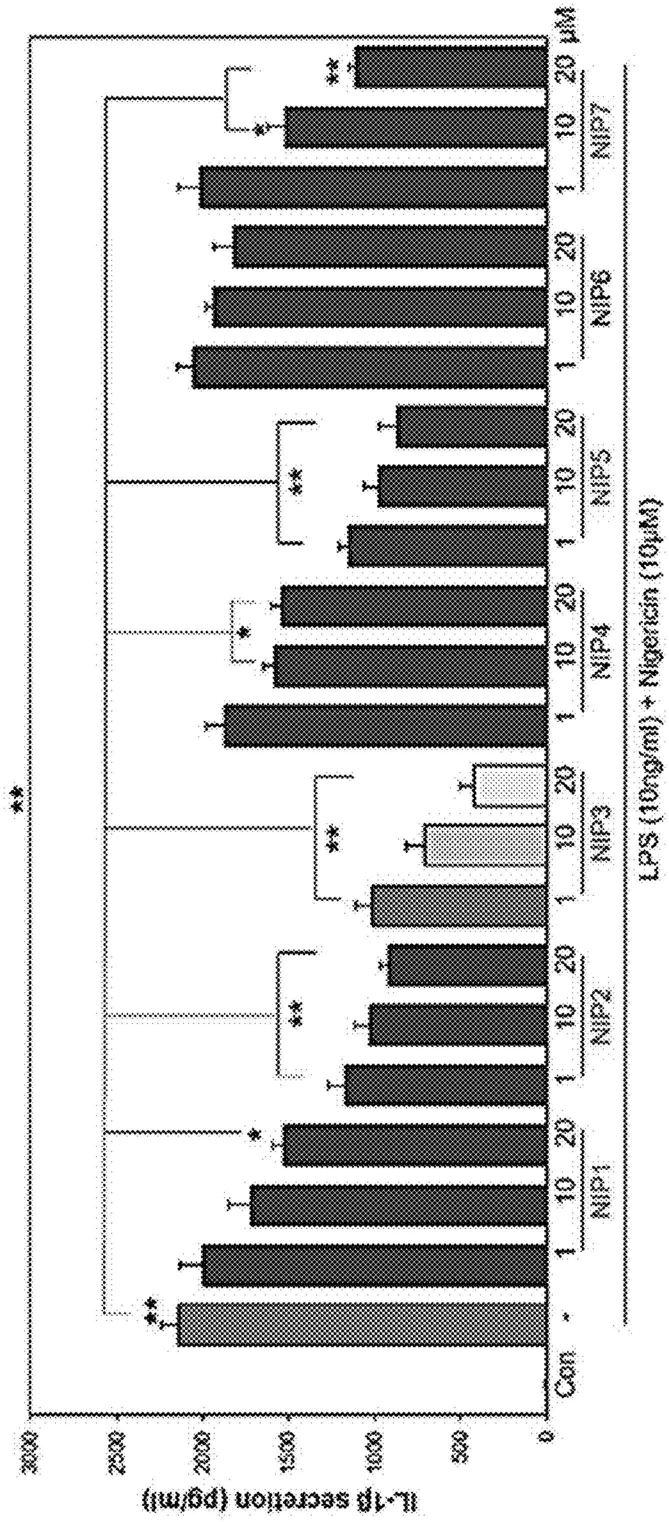
Figure 2A:
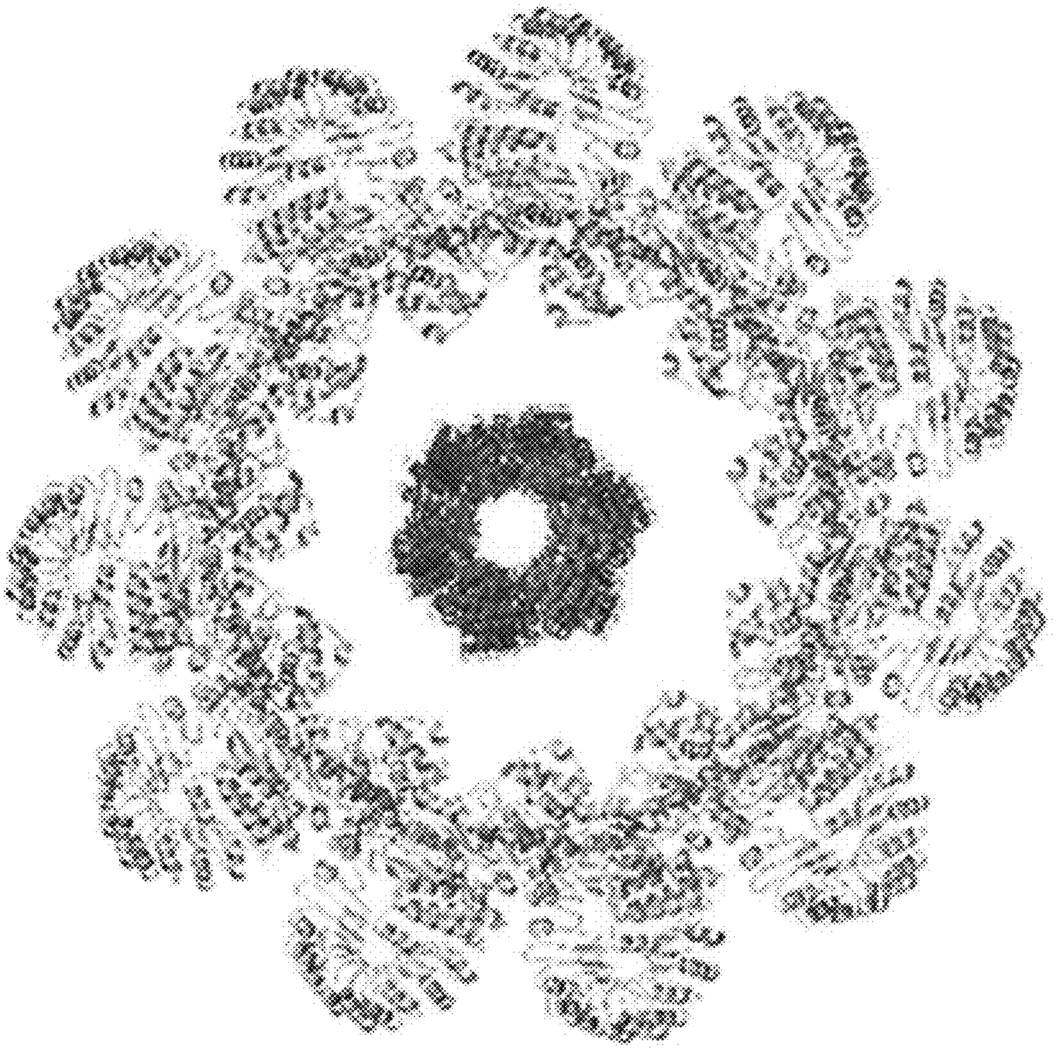
FIGS. 2A-2E show a docking complex model of the NLRP3 inflammasome assembly and NIP1 and NIP3, FIGS. 2A and 2B showing a top view and a lateral view of the inflammasome assembly, respectively, FIGS. 2C-2E showing NIP1-$ASC^{PYD}$ (FIG. 2C), NIP3-$ASC^{PYD}$ (FIG. 2D), and NIP3-$NLRP3^{PYD}$ (FIG. 2E) docking complexes, in which the electrostatic surfaces of $ASC^{PYD}$ and $NLRP3^{PYD}$ are represented.
Figure 2B:
Figure 2C:
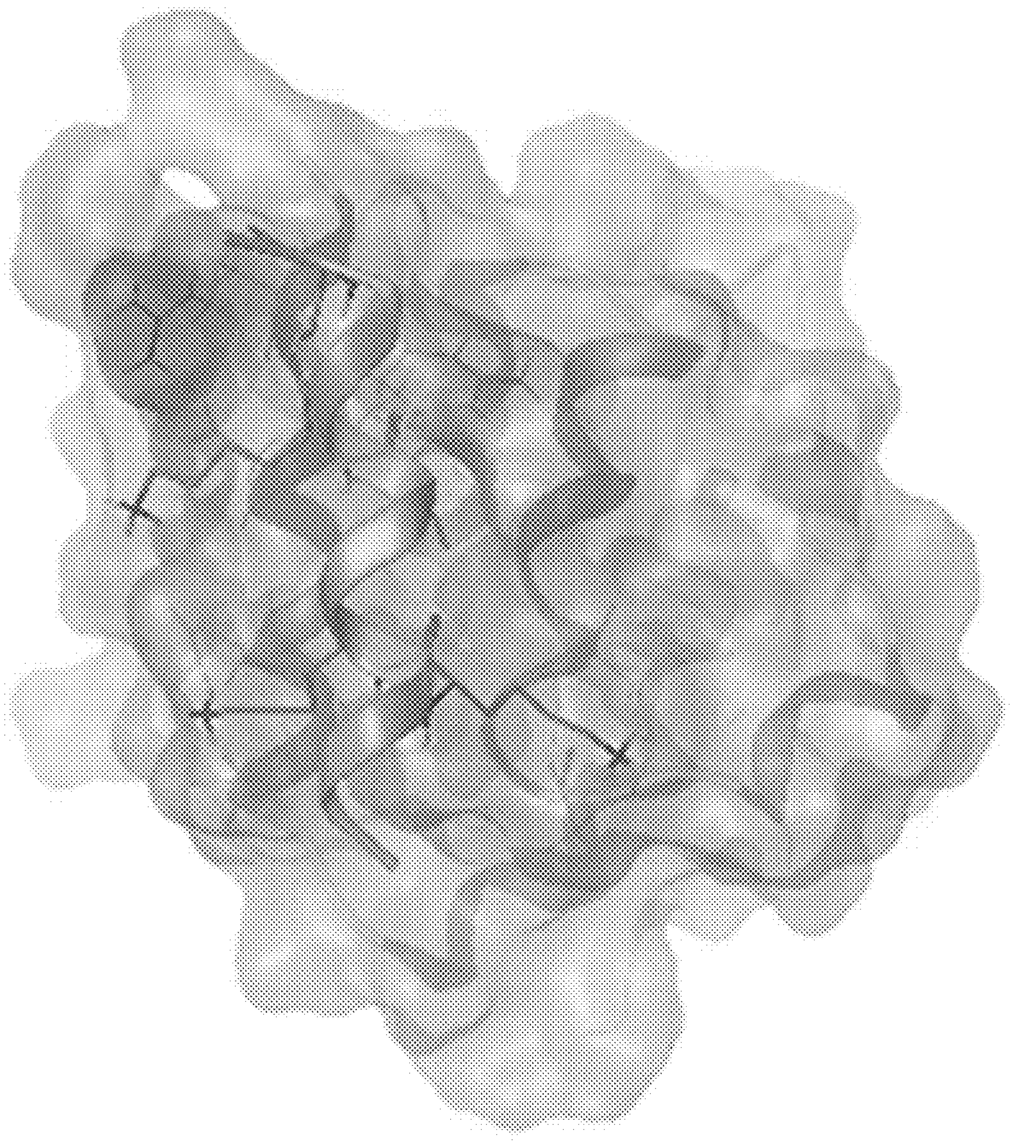
Figure 2D:
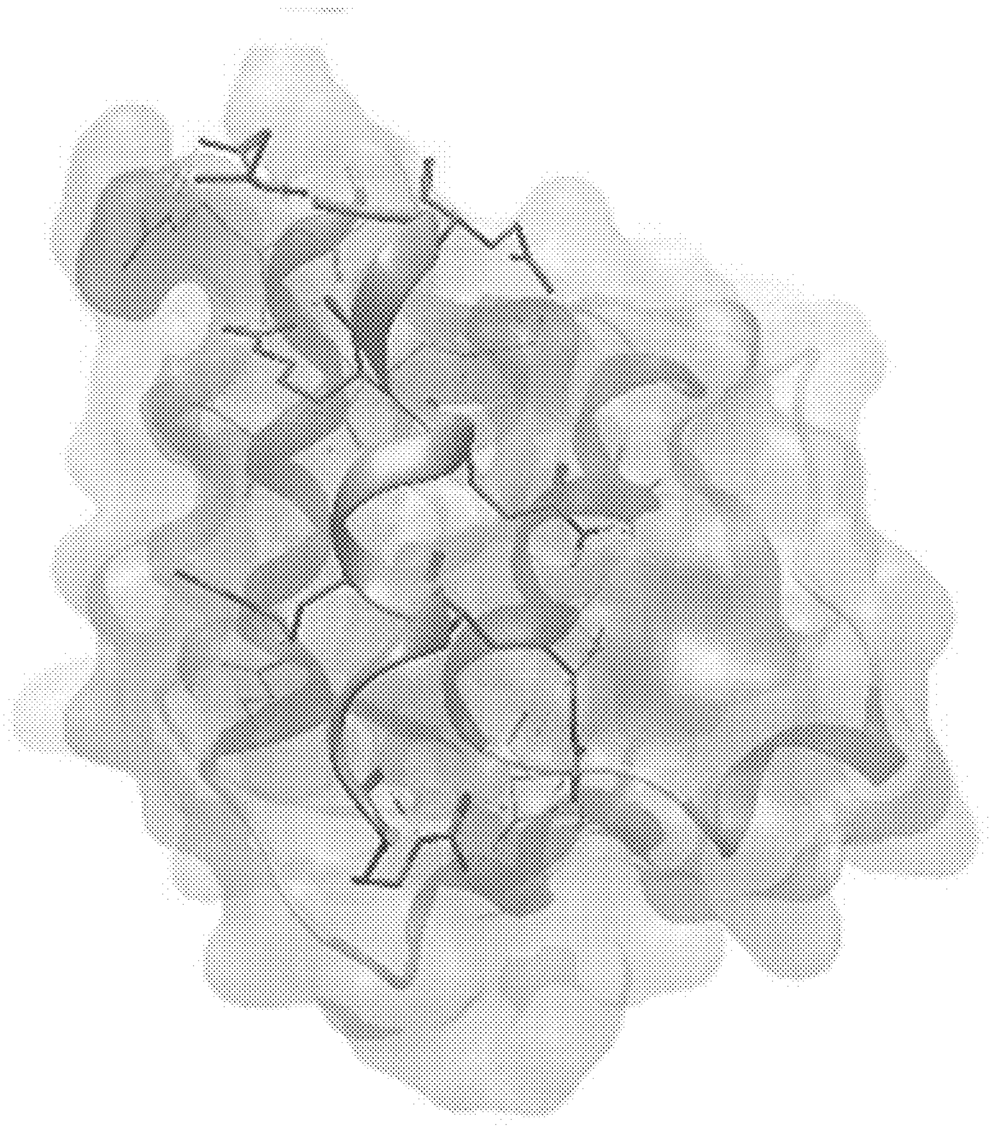
Figure 2E:
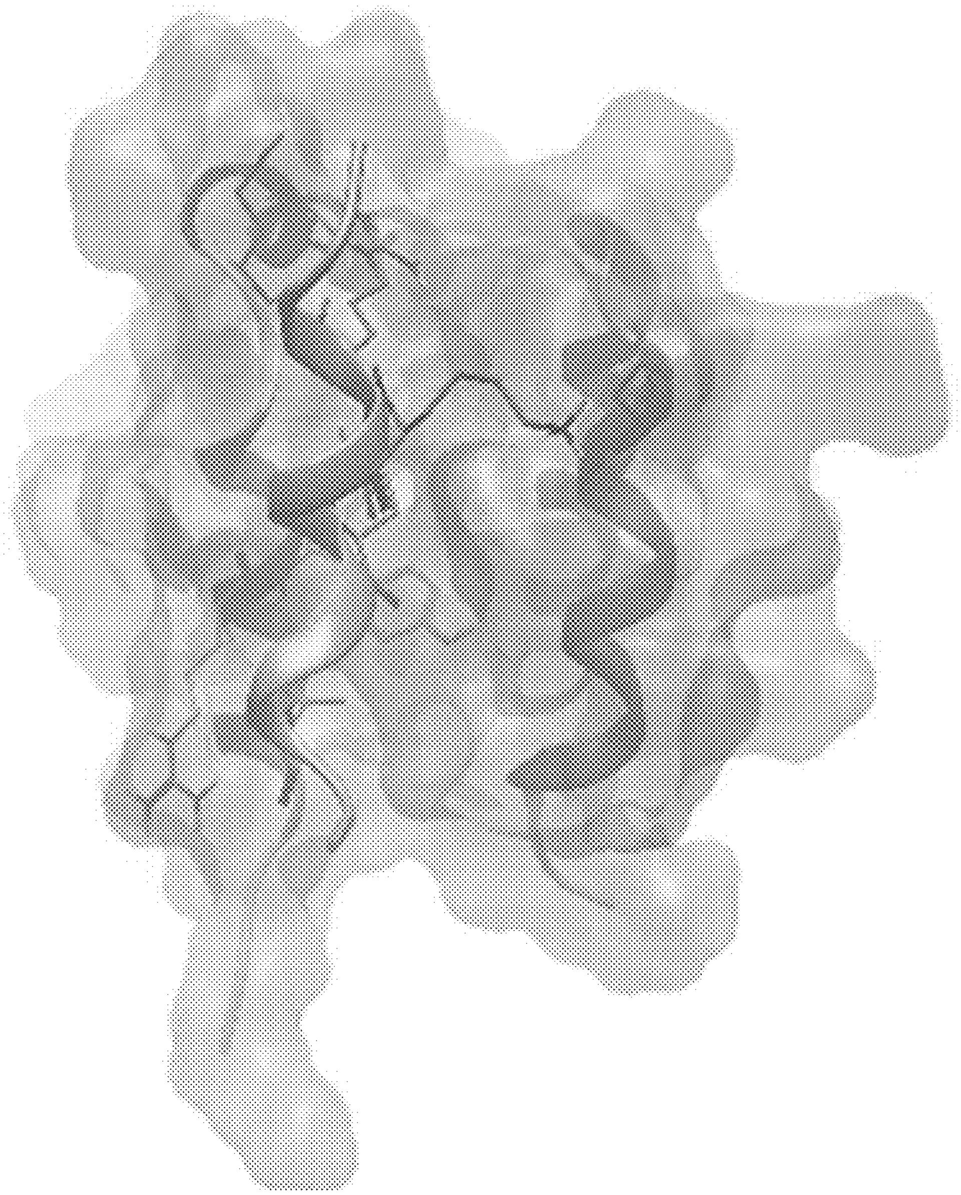
Figure 3A:
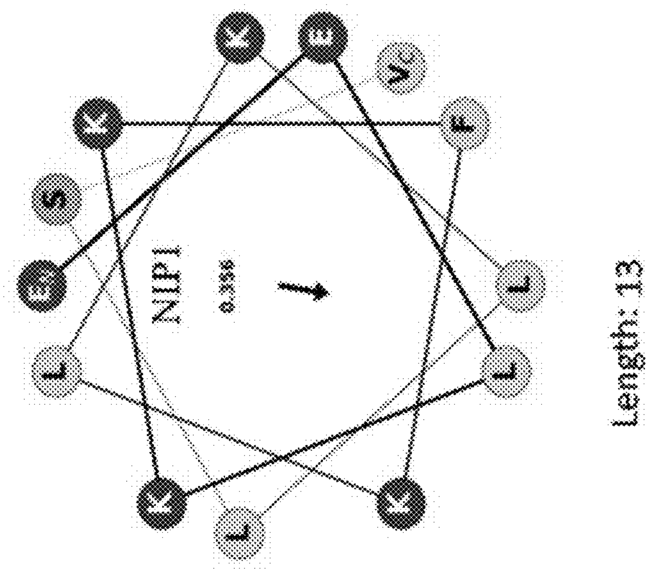
FIGS. 3A-3G show helical wheel plots of NIP, with positively charged residues, hydrophobic residues, and other residues highlighted in blue, red, yellow, and black, in which Eisenberg's hydrophobic moment for the idealized α-helical form is represented by an arrow with the corresponding value, and the length of each sequence is represented below the wheel.
Figure 3B:
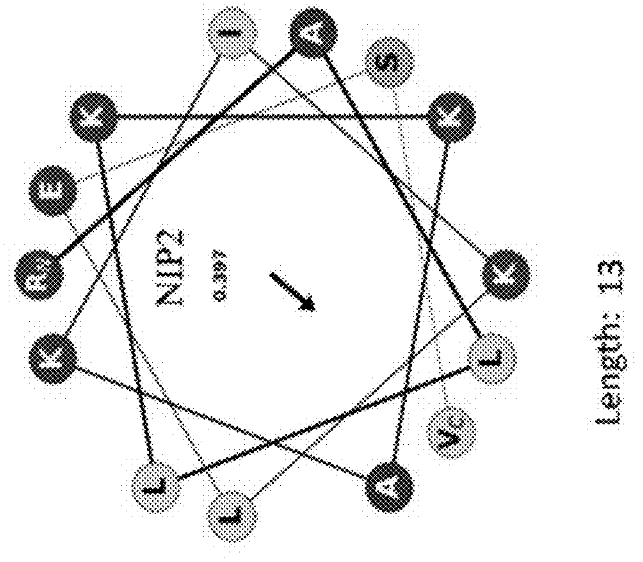
Figure 3D:
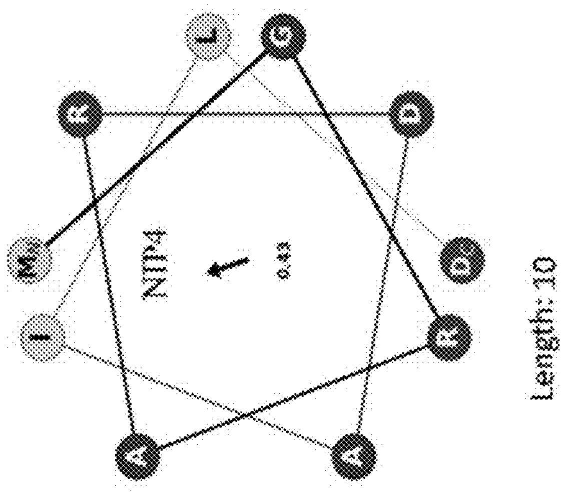
Figure 3C:
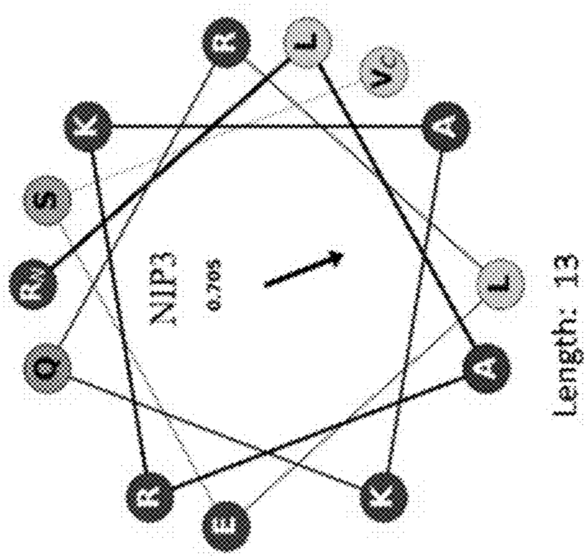
Figure 3E:
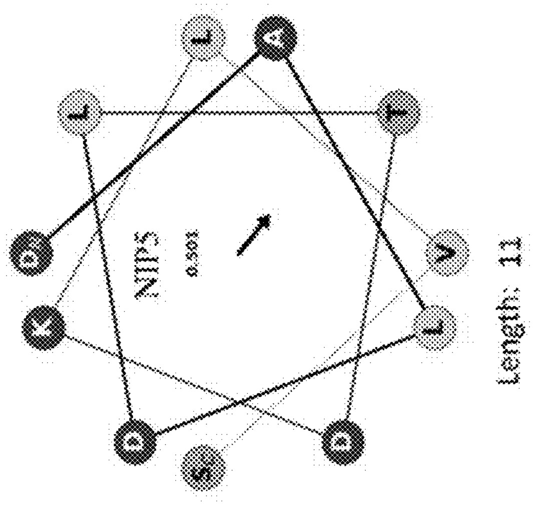
Figure 3F:
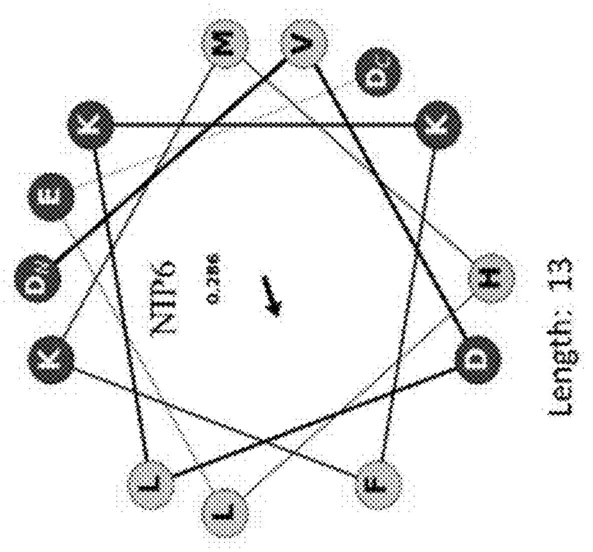
Figure 3G:
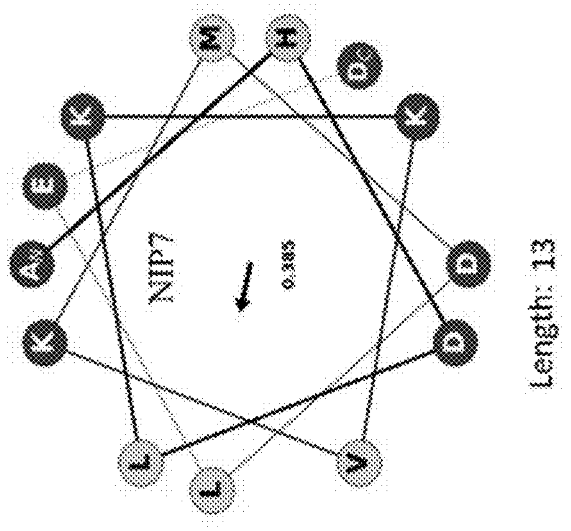

For inflammasome inhibition, to develop NLRP3 inhibitors that block $NLRP3^{PYD}$-$NLRP3^{PYD}$ PPI and $NLRP3^{PYD}$-$ASC^{PYD}$ PPI and inhibit activation of downstream signaling, the present inventors designed and screened a peptide library derived from the putative PYD-PYD interaction site of NLRP3 and ASC. NIP was derived from three PYD helices: NIP1-3 from the α2 helix of $ASC^{PYD}$, NIP4 from α4, NIP5 from α5, and NIP6 and NIP7 from the α2 helix of $NLRP3^{PYD}$. Screening of a library of NLRP3 inhibitors revealed that NIP3 potentially inhibits NLRP3 signaling in a dose-dependent manner. The region corresponding to NIP is located in PYD (FIGS. 1A-C). Two other NLRP3 peptides, NIP2 and NIP5, were found to moderately inhibit IL-1β and IL-18 expression (FIG. 1E).

$NLRP3^{PYD}$ has overall characteristics of the electrostatic surface similar to other ASC-binding PYDs such as $NLRP1^{PYD}$ and $ASC2^{PYD}$. Peptides (NIP6 and NIP7) derived from the $NLRP3^{PYD}$ domain with a structure homologous to $ASC^{PYD}$ did not have the ability to inhibit IL-1β and IL-18 secretion in a dose-dependent manner (FIG. 1E). $NLRP3^{PYD}$-derived peptide and $ASC^{PYD}$-derived peptide are structurally homologous with 50% sequence identity, but NIP6 and NIP7 cannot inhibit IL-1β and IL-18 secretion in a dose-dependent manner. The helicity of these peptides differs only slightly from that of NIP3 (FIG. 3). The sequences of $NLRP3^{PYD}$ and $ASC^{PYD}$ are highly conserved in PYD, with 6 out of 13 amino acid residues conserved in the α2 helix. NIP1 (derived from the α2 helix of $ASC^{PYD}$) and NIP6 (derived from the α2 helix of $NLRP3^{PYD}$) share about 50% homology. Therefore, the present inventors predicted that peptides derived from the α2 helix of other proteins would have similar properties. Although it is currently unclear to what extent this speculation applies to peptides derived from the PYD-PYD interface, available research data suggest that the binding conformation of protein-derived peptides often closely resembles the actual peptide conformation in folded proteins (P. Vanhee, et al., *Structure* 17, 1128-1136 (2009)).

Figure 4A:
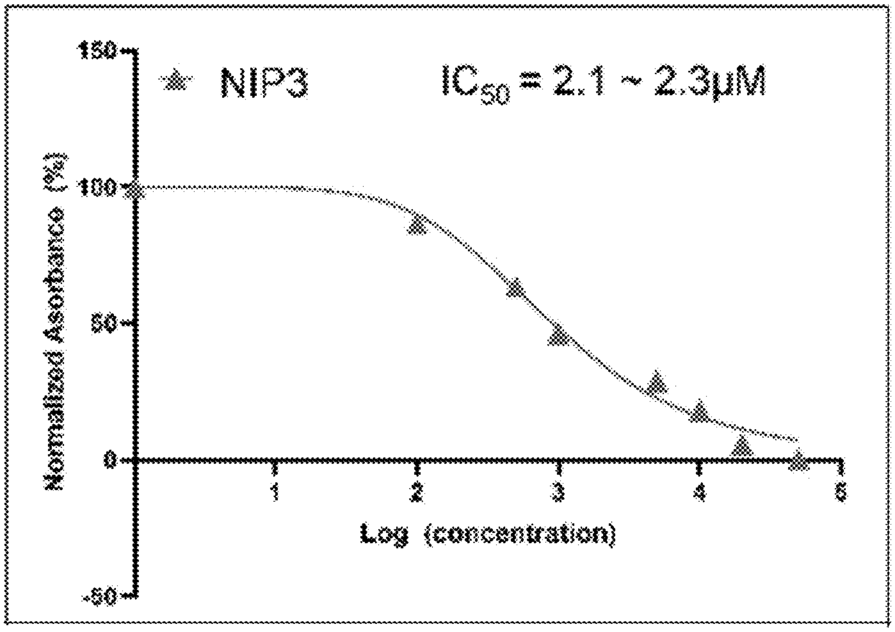
FIGS. 4A-4F show NIP3, which inhibits NLRP3-mediated signaling in THP1-derived macrophages.
Figure 4B:
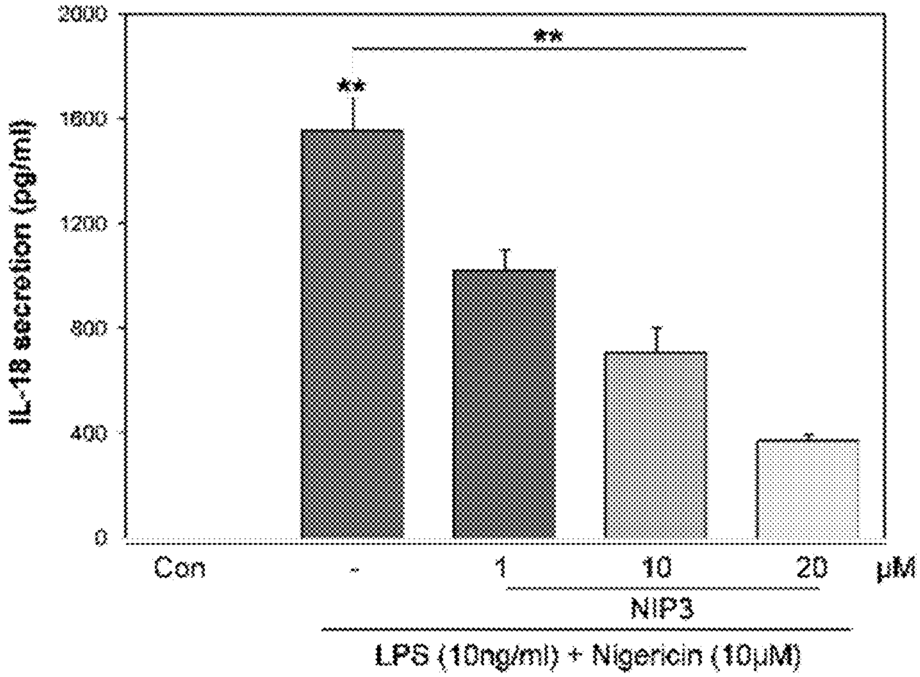

For reference, the peptide derived from $NLRP3^{PYD}$ is less potent than the $ASC^{PYD}$ peptide, and the $IC_{50}$ of NIP3 is 2.1-2.3 μM (FIG. 4A). In an embodiment of the present invention, binding energy data show that NIP3 has strong affinity for $ASC^{PYD}$, and this peptide has also been shown to have affinity for $NLRP3^{PYD}$. These results are consistent with NMR studies demonstrating the flexibility of the $NLRP3^{PYD}$ interface and the affinity of $ASC^{PYD}$, and this region binds to $NLRP3^{PYD}$ as previously reported (T. Srimathi, et al., *J. Biol. Chem.* 283, 15390-15398 (2008)). These results suggest that NIP3 binds to a variety of other proteins with similar affinity. Co-expression analysis of IL-8 and TNF-α with regard to the TLR4-mediated signaling pathway suggests that NIP3 inhibits NLRP3-mediated downstream signaling (FIGS. 4E and F).

Figure 4C:
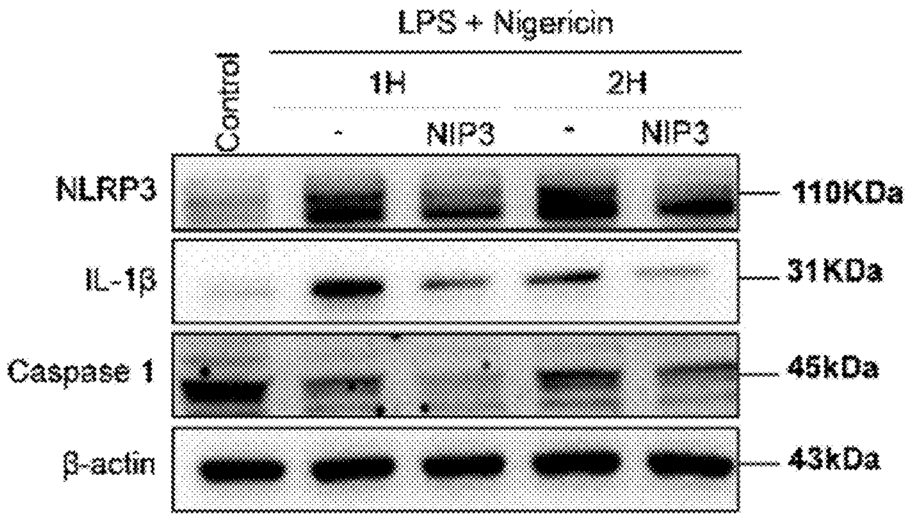
Figure 5:
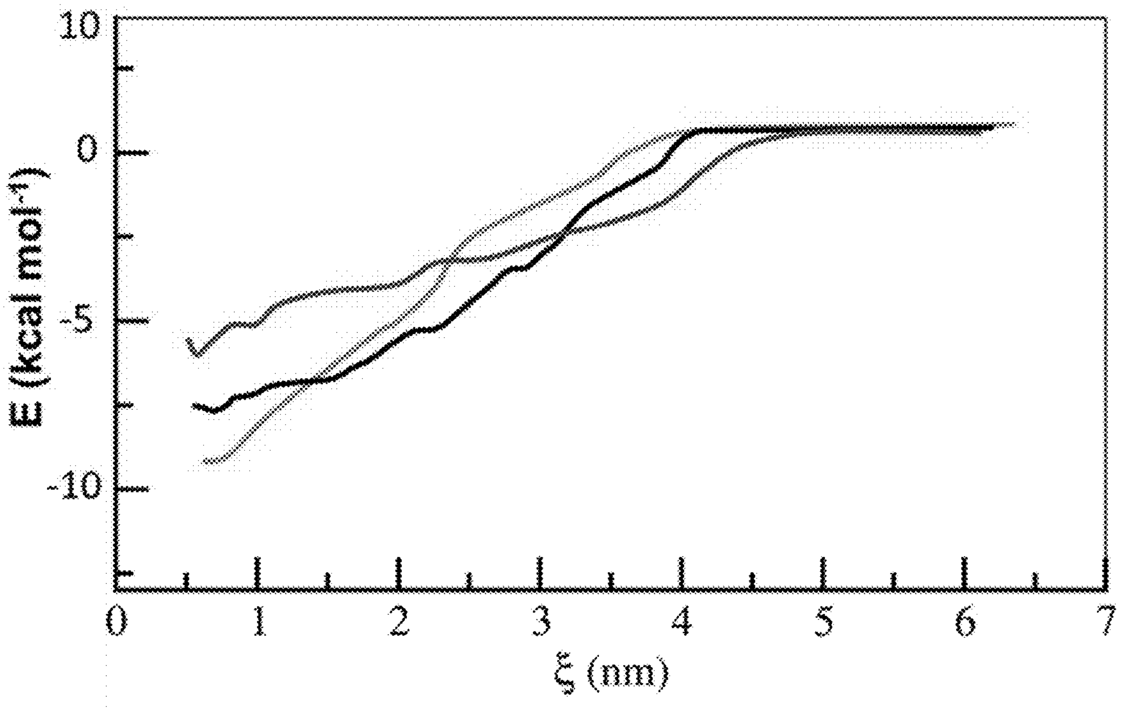
FIG. 5 shows PMF (potential mean force) curves for NIP1 and NIP3.

NIP3 interfered with NLRP3-mediated signaling and did not delay the secretion of cytokines TNF-α and IL-8 in the TLR4-mediated pathway of THP1-derived macrophages, which means that the peptide specifically inhibits NLRP3-mediated activation of IL-1β and IL-18 expression, as evidenced by Western blotting (FIG. 4C). The affinity values of NIP3 for PYD of NLRP3 and ASC as determined by the AA values (Table 3 and FIG. 5) are similar to the experimental data for ASC-ASC and ASC-NLRP3 interactions. Based on these results, it can be expected that NIP3 specifically binds to $ASC^{PYD}$ or $NLRP3^{PYD}$. NMR experiments on ASC revealed that ASC binds to both PYDs, indicating that $ASC^{PYD}$ self-association and interaction with $NLRP3^{PYD}$ are mediated by nearly identical binding domains (F. G. Bauernfeind, et al., *J. Immunol.* 183, 787-791 (2009)). NIP3-PYD binding prevents the continuation of a massive inflammatory response by disrupting intermolecular NLRP3-ASC oligomerization and $ASC^{PYD}$ self-association and nucleation. Either way, NLRP3 downstream signaling may be blocked by interfering with NLRP3 oligomerization, interaction with ASC through PYD, or both. Thus, maturation and pyroptosis of IL-1β and IL-18 are attenuated by inhibition of NLRP3 inflammasome assembly formation. Accordingly, NLRP3 associated with the pathogenesis of type 2 diabetes mellitus (H. Wen, et al., *Nat. Immunol.* 13, 352-357 (2012)), atherosclerosis (H. Zhang, et al., *Int. Immunopharmacol.* 77, 105934 (2019)), cardiovascular diseases (Z. Wang, et al., *Arterioscler Thromb. Vasc. Biol.* 38, 2765-2779 (2018)), and neurodegenerative diseases (S. Voet, et al., *EMBO Mol. Med.* 11, (2019)) may be inhibited by NIP3 treatment.

The use of peptides that inhibit PPI has become a promising way to develop active molecules. NIP3, with an $IC_{50}$ in the range of 2.1-2.3 μM, is a promising therapeutic agent for inhibiting the NLRP3 pathway. As demonstrated in in-vitro experiments, NIP3 has been identified as having the potential to alleviate inflammasome-related diseases. Moreover, NIP3 may be a good candidate for the development of peptidomimetics.

Accordingly, an aspect of the present invention pertains to a peptide comprising any one amino acid sequence selected from the group consisting of SEQ ID NO: 1 to SEQ ID NO: 7.

As used herein, the term "peptide" refers to a linear molecule formed by binding amino acid residues to each other by peptide bonding. The peptide may be prepared according to a chemical synthesis method known in the art.

In the present invention, the peptide is capable of down-regulating interleukin 1β (IL-1) and interleukin 18 (IL-18) by inhibiting NLRP3 inflammasome signaling.

The peptide is an NLRP3-ASC interface-mimicking peptide, defined as NIP (NLRP3/ASC-inhibitory peptide; NLRP3/ASC-inhibiting peptide), and the amino acid sequences of NIP1 to NIP7 are shown in Table 1 below.

TABLE 1

Amino acid sequences of NLRP3 inflammasome inhibitor NIP1-NIP7 peptides

| Name | Amino acid sequence | SEQ ID NO. |
|---|---|---|
| NIP1 | EELKKFKLKLLSV | 1 |
| NIP2 | RALKKAKIKLESV | 2 |
| NIP3 | RLARKAKQRLESV | 3 |
| NIP4 | DVDLKKFKMHLED | 4 |
| NIP5 | AHDLKKVKMDLED | 5 |

TABLE 1-continued

Amino acid sequences of NLRP3 inflammasome inhibitor NIP1-NIP7 peptides

| Name | Amino acid sequence | SEQ ID NO. |
|---|---|---|
| NIP6 | MGRARDAILD | 6 |
| NIP7 | DALDLTDKLVS | 7 |

The peptide according to the present invention is understood to include variants or fragments thereof in which an amino acid residue is conservatively substituted at a specific amino acid residue position.

As used herein, "conservative substitution" refers to a modification that includes substituting one or more amino acids with amino acids having similar biochemical properties that do not cause loss of biological or biochemical functions of the corresponding peptide.

A "conservative amino acid substitution" is a substitution in which an amino acid residue is replaced with an amino acid residue having a similar side chain. Classes of amino acid residues with similar side chains have been defined in the art and are well known. These classes include amino acids with basic side chains (e.g. lysine, arginine, histidine), amino acids with acidic side chains (e.g. aspartic acid, glutamic acid), amino acids with uncharged polar side chains (e.g. glycine, asparagine, glutamine, serine, threonine, tyrosine, cysteine), amino acids with non-polar side chains (e.g., alanine, valine, leucine, isoleucine, proline, phenylalanine, methionine, tryptophan), amino acids with beta-branched side chains (e.g. threonine, valine, isoleucine), and amino acids with aromatic side chains (e.g. tyrosine, phenylalanine, tryptophan, histidine).

It is expected that the NIP1 to NIP7 peptides of the present invention may still retain activity even with conservative amino acid substitutions.

The peptide according to the present invention has substantially the same function and/or effect as the peptide, and is also understood to include peptides having amino acid sequence homology of 80% or 85% or more, preferably 90% or more, more preferably 95% or more, most preferably 99% or more with the amino acid sequence of SEQ ID NO: 1 to SEQ ID NO: 7.

Another aspect of the present invention pertains to a fusion peptide in which the peptide and a cell-penetrating peptide (CPP) are conjugated.

As used herein, the term "cell-penetrating peptide (CPP)" is a kind of signal peptide, and is a peptide that is a combination of specific amino acid sequences used for the purpose of delivering macromolecules such as proteins, DNA, RNA, etc. into cells. To date, cell-penetrating peptides have been used for intracellular delivery of various small compounds, and macromolecules such as proteins, peptides, RNA, DNA, etc. Most cell-penetrating peptides are derived from protein transduction domains (PTDs) or membrane-translocating sequences, move into cells without damaging cell membranes, unlike general entry routes of foreign materials into cells, and are considered to play a revolutionary role in delivering DNA or proteins, which are known to be unable to pass through cell membranes, into cells.

The fusion peptide of the present invention uses a cell-penetrating peptide, and the cell-penetrating peptide is not particularly limited so long as it is able to enter cells by an endocytosis mechanism, but is preferably selected and used from the group consisting of cell-penetrating peptides or variants thereof listed in Table 2 below.

TABLE 2

| Peptide | References | Sequence | SEQ ID NO. |
|---|---|---|---|
| TAT | Takeshima et al., (2003) J. Biol. Chem. 278(2), 1310-1315 | YGRKKRRQRRR | 8 |
| $TAT_{(48-60)}$ | Dennison et al., (2007) Biochem. and Biophy. Res. Comm. 363, 178 | GRKKRRQRRRPPQ | 9 |
| $TAT_{(49-57)}$ | Baoum et al., (2012) Int. J. Pharm. 427, 134-142 | RKKRRQRRR | 10 |
| Penetratin | Derossi et al., (1994) J. Biol. Chem. 269(14), 10444-10450 | RQIKIWFQNRRMKWKK | 11 |
| R8 | Chu et al., (2015) Nanotechnol. Biol. Med. 11, 435-446 | RRRRRRRR | 12 |
| R9-TAT | Futaki et al., (2001) J. Biol. Chem. 276, 5836-5840 | GRRRRRRRRRPPQ | 13 |
| Pep-1 | Deshayes et al., (2008) Advanced Drug Delivery Reviews, 60, 537-547 | KETWWETWWTEWSQPKKKRKV | 14 |
| Hph-1 | Choi et al., (2006) Nat. Med. 12, 574-579. | YARVRRRGPRR | 15 |
| MAP | Wada et al., (2013) Bioorg. Med. Chem. 21, 7669-7673 | KLALKLALKALKAALKLA | 16 |
| pVEC | Elmquist et al., (2006) Biochim. Biophys. Acta. 1758, 721-729 | LLIILRRRIRKQAHAHSK | 17 |

TABLE 2-continued

| Peptide | References | Sequence | SEQ ID NO. |
|---|---|---|---|
| MPG | Simeoni, (2003) Nucleic Acids Res. 31, 2717-2724 | GALFLGFLGAAGSTMGA WSQPKKKRKV | 18 |
| Transportan | Pae et al., (2014) J. Controlled Release, 192, 103-113 | GWTLNSAGYLLGKINLKA LAALAKKIL | 19 |
| gH625 | Galdiero et al., (2015) Biochim. Biophys. Acta (BBA) Biomembr. 1848, 16-25. | HGLASTLTRWAHYNALIR AF | 20 |
| VP22 | Elliott and O'Hare (1997) Cell, 88, 223-233 | NAKTRRHERRRKLAIER | 21 |

In an embodiment of the present invention, an experiment was performed by selecting penetratin represented by the amino acid sequence of SEQ ID NO: 11, and even when other cell-penetrating peptides, rather than the cell-penetrating peptide actually used, were fused with the peptide of the present invention, effects similar to the present invention appeared, as will be obvious to those skilled in the art.

In the present invention, the peptide and the cell-penetrating peptide may be connected directly or through a linker.

In an embodiment of the present invention, a peptide comprising any one amino acid sequence selected from the group consisting of SEQ ID NO: 1 to SEQ ID NO: 7 was effective at inhibiting the secretion of IL-1β and IL-18, which are key components of NLRP3 inflammasome signaling, and at inhibiting the expression of caspase-1, thereby suppressing NLRP3 inflammasome activity.

Accordingly, still another aspect of the present invention pertains to a composition for inhibiting NLRP3 inflammasome activity comprising the peptide or the fusion peptide.

As used herein, the term "inhibition" refers to a phenomenon in which biological activity or signaling activity is deteriorated due to deficiency, incompatibility, or many other causes, and the activity of NLRP3 may be partially or completely blocked, reduced, prevented, delayed, inactivated, or downregulated.

As used herein, the term "inhibitor" refers to a molecule that partially or completely inhibits the effect of other molecules such as receptors or intracellular mediators by any mechanism. In the present specification, the composition for inhibiting NLRP3 inflammasome is used in the same sense as the NLRP3 inflammasome inhibitor. In the present invention, the inhibition of inflammasome activity indicates an in-vivo transformation that causes a decrease in inflammasome activation in a target cell, etc., and for the purpose of the present invention, the inhibition may be inhibition of $NLRP3^{PYD}$-$ASC^{PYD}$ oligomerization and $ASC^{PYD}$-$ASC^{PYD}$ self-association, inhibition of NLRP3 inflammasome assembly, or inhibition of cytokine production due to inflammasome. Preferably, the peptide is able to inhibit inflammasome activity by interfering with $NLRP3^{PYD}$-$ASC^{PYD}$ interaction and $ASC^{PYD}$-$ASC^{PYD}$ self-association through strong binding to $ASC^{PYD}$ and $NLRP3^{PYD}$ but the present invention is not limited thereto.

In an embodiment of the present invention, since the peptide inhibits the secretion of pro-inflammatory cytokines related to NLRP3 inflammasome signaling, it may be efficiently used for a composition for preventing or treating an NLRP3 inflammasome-related inflammatory disease.

Accordingly, yet another aspect of the present invention pertains to a composition for preventing or treating an NLRP3 inflammasome-related inflammatory disease comprising the peptide or the fusion peptide.

Still yet another aspect of the present invention pertains to a method of preventing or treating an NLRP3 inflammasome-related inflammatory disease comprising administering the peptide or the fusion peptide.

A further aspect of the present invention pertains to the use of the peptide or the fusion peptide for the prevention or treatment of an NLRP3 inflammasome-related inflammatory disease.

Still a further aspect of the present invention pertains to the use of the peptide or the fusion peptide for the manufacture of a medicament for the prevention or treatment of an NLRP3 inflammasome-related inflammatory disease.

In the present invention, the NLRP3 inflammasome-related inflammatory disease is an abnormal disease that occurs when the inflammasome is abnormally and excessively activated, and preferable examples thereof include, but are not limited to, metabolic diseases including diabetes, atherosclerosis, metabolic syndrome, cardiovascular diseases, and neurodegenerative diseases, neuroinflammatory diseases, and autoinflammatory diseases.

In the present invention, the metabolic disease refers to a disease caused by metabolic disorders in vivo, preferably obesity, hyperlipidemia, hypercholesterolemia, arteriosclerosis, type 2 diabetes mellitus, nonalcoholic fatty liver disease (NAFLD), or nonalcoholic steatohepatitis (NASH), more preferably type 2 diabetes mellitus or arteriosclerosis, but is not limited thereto.

According to a recent study, increased NLRP3 protein expression was confirmed in adipocytes of obese patients, and ceramide synthesized in obese adipocytes was found not only to activate the NLRP3 inflammasome, but also to greatly reduce the incidence of type 2 diabetes mellitus in the absence of inflammasome activity in NLRP3 gene-deficient mice (Ryan W. Grant and Vishwa D. Dixit, *Front Immunol.* 2013: 4: 50). In addition, a high incidence of atherosclerosis has been reported in patients with hyperlipidemia when inflammation occurs in blood vessels, and it has been found that inflammatory cells recognize cholesterol crystals and induce the formation and synthesis of NLRP3 inflammasome to thus increase the inflammatory response of blood vessels (Peter Duewell, et al., *Nature.* 2010 Apr. 29:464(7293): 1357-61). Therefore, the NLRP3 inflammasome plays a very important role in inducing and/or promoting the metabolic disease.

In the present invention, the neuroinflammatory disease refers to a disease caused by damage to nerve tissue by an inflammatory response. The neuroinflammatory disease is preferably Alzheimer's disease, gout, Parkinson's disease, Huntington's disease, Lou Gehrig's disease, Creutzfeldt-Jakob disease, multiple sclerosis, amyotrophic lateral sclerosis, diffuse Lewy body disease, leukoencephalitis, temporal lobe epilepsy, or inflammatory spinal cord injury, more preferably Alzheimer's disease, but is not limited thereto.

In case of Alzheimer's disease, inflammasome activation of microglia has been reported as an important mechanism, and in an animal model of Alzheimer's disease, the amounts of cytokines caspase-1 and IL-1 generated by inflammasome in microglia are increased (Emily L. Goldberg and Vishwa Deep Dixit, Immunol. Rev. 2015 May: 265(1):63-74).

In the present invention, the autoinflammatory disease is classified as a group of diseases in which systemic inflammation is frequently repeated in a state where autoantibodies or antigen-specific T cells are not found, unlike autoimmune diseases, and is characterized mainly as resulting from dysregulation of innate immunity (Journal of Rheumatic Disease Vol. 21. No. 5. October 2014). Preferable examples thereof include, but are not limited to, Muckle-Wells syndrome (MWS), latent autoimmune diabetes in adults (LADA), familial cold autoinflammatory syndrome (FCAS), cryopyrin-associated periodic syndrome (CAPS), neonatal-onset multisystem inflammatory disease (NOMID), chronic infantile neurologic cutaneous and articular (CINCA) syndrome, familial Mediterranean fever (FMF), certain forms of juvenile arthritis such as systemic juvenile idiopathic arthritis (SJIA), certain forms of juvenile rheumatoid arthritis such as systemic juvenile idiopathic rheumatoid arthritis, and certain forms of adult rheumatoid arthritis.

As used herein, the term "prevention" refers to any action that inhibits or delays an NLRP3 inflammasome-related inflammatory disease by administering a pharmaceutical composition comprising the peptide or the fusion peptide. In addition, the term "treatment" used herein refers to any action in which the symptoms of an NLRP3 inflammasome-related inflammatory disease are alleviated or eliminated by administrating a pharmaceutical composition comprising the peptide or the fusion peptide.

The composition for preventing or treating an NLRP3 inflammasome-related inflammatory disease according to the present invention may comprise a pharmaceutically effective amount of the peptide or the fusion peptide alone, or may also comprise one or more pharmaceutically acceptable carriers, excipients, or diluents. Here, the pharmaceutically effective amount is an amount sufficient to prevent, ameliorate, or treat the symptoms of an NLRP3 inflammasome-related inflammatory disease.

The term "pharmaceutically acceptable" refers to a composition that is physiologically acceptable and does not normally cause allergic reactions such as gastrointestinal disorders and dizziness or similar reactions when administered to humans. Examples of the carriers, excipients, and diluents may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil. Also, fillers, anticoagulants, lubricants, wetting agents, fragrances, emulsifiers, and preservatives may be further included.

The term "carrier" refers to a material that facilitates the delivery of a compound into a cell or tissue.

The term "diluent" is defined as a material that stabilizes the biologically active form of the compound of interest and is diluted with water in which the compound is dissolved.

Also, the composition of the present invention may comprise at least one known active ingredient having a therapeutic effect on an NLRP3 inflammasome-related inflammatory disease, in addition to the peptide or the fusion peptide.

The composition of the present invention may be formulated using methods known in the art to provide rapid, sustained, or delayed release of the active ingredient after administration to a mammal other than a human. Formulations may be in the form of powders, granules, tablets, emulsions, syrups, aerosols, soft or hard gelatin capsules, sterile injectable solutions, or sterile powders.

The composition of the present invention may be administered through various routes including oral, transdermal, subcutaneous, intravenous, or intramuscular routes, and the dosage of the active ingredient may be appropriately determined depending on various factors, such as the route of administration, and the patient's age, gender, body weight, and the severity of disease, and the composition according to the present invention may be administered in combination with a known compound having an effect of preventing, ameliorating, or treating the symptoms of an NLRP3 inflammasome-related inflammatory disease.

Yet a further aspect of the present invention pertains to a food composition for preventing or ameliorating an NLRP3 inflammasome-related inflammatory disease comprising the peptide or the fusion peptide.

The term "amelioration" is not limited so long as it is any action that alleviates or beneficially changes the symptoms of a metabolic disease, a neuroinflammatory disease, or an autoinflammatory disease using the food composition of the present invention.

In the present invention, the food composition is preferably a health functional food, and may be a food additive. The health functional food or food additive is preferably a powder, granule, tablet, capsule, or beverage, but is not limited thereto.

The food of the present invention may comprise the peptide or the fusion peptide according to the present invention alone or in combination with other foods or food ingredients, which may be appropriately used according to a typical method.

There is no particular limitation on the type of food. Examples of the food to which the peptide or the fusion peptide according to the present invention may be added include meat, sausage, bread, chocolate, candy, snacks, confectionery, pizza, ramen, other noodles, gum, dairy products including ice cream, various soups, beverages, tea, drinks, alcoholic beverages, and vitamin complexes, and include all foods in a typical sense.

The food composition of the present invention may be a beverage composition. The beverage composition may comprise various flavoring agents or natural carbohydrates as additional ingredients, like typical beverages. The aforementioned natural carbohydrates include monosaccharides such as glucose and fructose, disaccharides such as maltose and sucrose, and polysaccharides, for example, dextrin and cyclodextrin, or sugar alcohols such as xylitol, sorbitol, and erythritol. As the sweetener, natural sweeteners such as thaumatin and *stevia* extract, or synthetic sweeteners such as saccharin and aspartame may be used.

The food composition of the present invention may comprise the peptide or the fusion peptide as an essential ingredient and various herbal extracts, supplementary food additives, or natural carbohydrates as additional ingredients. Moreover, supplementary food additives may be further added, and supplementary food additives include typical supplementary food additives in the art, for example, flavoring agents, flavors, colorants, fillers, stabilizers, and the like. Examples of the natural carbohydrates include monosaccharides such as glucose, fructose, and the like, disaccharides such as maltose, sucrose, and the like, and polysaccharides, for example, typical sugars such as dextrin, cyclodextrin, and the like, and sugar alcohols such as xylitol, sorbitol, erythritol, and the like. As flavoring agents other than those mentioned above, natural flavoring agents (thaumatin, *stevia* extract (e.g. rebaudioside A, glycyrrhizin, etc.)) and synthetic flavoring agents (saccharin, aspartame, etc.) may advantageously be used. In addition to the above, the food composition of the present invention may comprise various nutrients, vitamins, minerals (electrolytes), flavors such as synthetic flavors and natural flavors, colorants, enhancers (cheese, chocolate, etc.), pectic acid and salts thereof, alginic acid and salts thereof, organic acids, protective colloidal thickeners, pH adjusting agents, stabilizers, preservatives, glycerin, alcohols, carbonating agents used in carbonated beverages, and the like. Also, the food composition of the present invention may comprise fruit flesh for the manufacture of natural fruit juice, fruit juice beverages, and vegetable beverages. These components may be used independently or in combination. The proportions of these additives are not very important, but are generally selected in the range of 0.01 to 0.1 parts by weight based on 100 parts by weight of the composition of the present invention.

A better understanding of the present invention may be obtained through the following examples. These examples are merely set forth to illustrate the present invention, and are not to be construed as limiting the scope of the present invention, as will be obvious to those skilled in the art.

Example 1: Materials and Methods

Example 1-1: Computational Design of Peptides Through Interface Analysis

NLRP3 contains leucine-rich repeats, a nucleotide binding domain, and PYD, while ASC contains PYD and CARD, and caspase-1 contains CARD and a caspase domain. NLRP3, ASC, and caspase-1 constitute an inflammasome assembly. This assembly includes the PYD-PYD interaction between NLRP3 and ASC and the CARD-CARD interaction between ASC and caspase-1. Both NLRP3 and ASC self-associate. A structural model of the NLRP3 inflammasome assembly was constructed in MOE software using NLRP3, $NLRP3^{PYD}$, and $ASC^{PYD}$ retrieved from the RCBS Protein Data Bank (PDB). Two sets of peptides were designed from NLRP3- and ASC-interacting domains. The structures of NLRP3 (PDB ID: 6NPY), $NLRP3^{PYD}$ (PDB ID: 2NAQ), and $ASC^{PYD}$ (PDB ID: 3J63) were retrieved from the RCSB PDB. Then, a model of the $NLRP3^{PYD}$-$ASC^{PYD}$ heterodimer was constructed. The α2 helix of $NLRP3^{PYD}$ interacts with $ASC^{PYD}$, and the α2 helix in the ASC PYD-PYD dimer interacts with the al and α4 helices of other $ASC^{PYD}$ monomers. Peptides were designed using these data and model structures. Peptides were mutated in silico (via computer simulation) using MOE software at various locations and models were refined. The helicity and hydrophobicity of the designed peptides were determined using the helical wheel plot of the Python-based software modlAMP (A. T. Muller, et al., *Bioinformatics* 33, 2753-2755 (2017)). After model optimization and refinement, based on the stability and affinity scores, molecular dynamics simulations were performed for NIP for detailed structural and energetic analysis. In order to promote uptake of NIP by cells, the peptide was fused with a cell-penetrating peptide called penetratin (RQIKIWFQNRRMKWKK: SEQ ID NO: 11) at the N-terminus thereof.

Examples 1-2: Peptide Synthesis and Cell Culture

NIP was synthesized by Peptron (Ansan, Korea) with a purity of 96% or more, as determined by reverse-phase high-performance liquid chromatography (Shimadzu Prominence). THP1-derived macrophages were used for in-vitro screening of peptides. Cells were cultured in RPMI 1640 medium supplemented with 1% penicillin/streptomycin solution and 10% fetal bovine serum (FBS: Thermo Fisher Scientific, Inc., Waltham, MA, USA). THP1 cells were differentiated into macrophages for 24 hours using 80 nM phorbol 12-myristate 13-acetate (Sigma-Aldrich Co., St. Louis, MO, USA). The cells were cultured in a humidified environment containing 5% $CO_2$ at 37° C. (Thermo Fisher Scientific, Inc.), and the medium was replaced after 18 hours of culture.

Examples 1-3: Cell Viability Assay

THP1 cells were seeded at 105/well and grown overnight in a 96-well plate (BD Biosciences, San Jose, CA, USA). Cell viability was measured by colorimetric 1-(4,5-dimethylthiazol-2-yl)-3,5-diphenylformazan (MTT) assay (Sigma-Aldrich).

Examples 1-4: ELISA (Enzyme-Linked Immunosorbent Assay) and Cell Processing

THP1-derived macrophages were seeded at a density of 105/well in a 96-well plate (BD Biosciences) and grown overnight. The next day, the cells were primed with LPS (Sigma-Aldrich) at a concentration of 10 ng/ml or human tumor necrosis factor alpha (TNF-α; R&D Systems, Minneapolis, Minn., USA) at a concentration of 100 ng/ml for 3 hours, and then treated with peptides at different concentrations for 1 hour. In order to activate the NLRP3 pathway, LPS-primed cells were stimulated for 2 hours with 10 M nigericin (Invivogen, Carlsbad, CA, USA), which is a known NLRP3 activator. After 6 hours of treatment, the secretion levels of IL-1β and IL-18 were evaluated using a Human IL-1β Uncoated ELISA Kit (Invitrogen) and a Human IL-18 ELISA kit (RayBiotech, Norcross, GA, USA), respectively. The secretion levels of IL-8 and TNF-α were analyzed using a Human IL-8 ELISA kit and a TNF-α ELISA Kit (Invitrogen), respectively. In all experiments, absorbance was analyzed at an appropriate wavelength using a microplate spectrophotometry system (Molecular Devices Inc., Silicon Valley, CA, USA).

Examples 1-5: Protein Quantification and Western Blotting

Total protein extraction was performed using an M-PER Mammalian Protein Extraction Reagent (Thermo Fisher Scientific, Inc.). Total protein was measured using a bicinchoninic acid (BCA) assay kit (Sigma-Aldrich). Western blotting including gel electrophoresis and transfer was performed on a Mini-PROTEAN Tetra Cell and Mini Trans-Blot Electrophoretic Transfer Cell System (Bio-Rad Laboratories, Hercules, CA, USA). Membranes were immunoblotted with the following specific primary antibodies at a 1:1000 dilution with gentle shaking at 4° C. overnight. Antibodies against IL-1β and NLPR3 were purchased from Cell Signaling Technology Inc. (Danvers, MA, USA), and antibodies against β-actin and caspase-1 were purchased from Santa Cruz Biotechnology Inc. (Dallas, TX, USA). The next day, all membranes were thoroughly washed with phosphate-buffered saline (PBS) supplemented with 0.1% Tween 20, followed by culture for 2 hours with peroxidase-conjugated anti-mouse or anti-rabbit IgG antibodies (1:1,000). Proteins were detected with a SuperSignal West Pico ECL solution (Thermo Fisher Scientific, Inc.) and visualized with a ChemiDoc™ Touch Imaging System (Bio-Rad Laboratories).

Examples 1-6: Umbrella Sampling Simulation

COM analysis and umbrella sampling simulation were performed to calculate the binding energy and affinity of the designed NIP to $ASC^{PYD}$ and $NLRP3^{PYD}$. In the present invention, umbrella sampling simulation has access to sufficient timescales to achieve adequate sampling of the binding process and is thus advantageous over all-atom molecular dynamics simulations. Peptide-protein complexes were equilibrated by all-atom simulations before generation of molecular topology for umbrella sampling. Clustering was performed after equilibration. Frames from clusters occupying the most space with the smallest root mean square deviation were selected for umbrella sampling. A series of arrays was created along a single reaction coordinate, and frames were extracted from the trajectories corresponding to the desired COM intervals. Umbrella sampling simulation was performed for each array and limited within the selected COM distance. A weighted histogram analysis method was used to determine PMF for calculating ΔG.

Examples 1-7: Statistical Analysis

All data analysis was performed by t test in SigmaPlot software (12.0 version: Systat Software Inc., San Jose, CA, USA) or GraphPad Prism 5 (GraphPad Software, Inc., San Diego, CA, USA). All experiments were performed independently at least 4 times, and statistical significance was defined as P value<0.05 or <0.01.

Example 2: NIP (NLRP3/ASC-Inhibitory Peptide) Candidate Design

When the amino terminus of $NLRP3^{PYD}$ recruits caspase-1 through homotypic interaction with $ASC^{PYD}$, the NLRP3 inflammasome is assembled and pro-inflammatory cytokines are then released. In particular, PYD oligomerization is required for inflammasome assembly. PYD-PYD dimer interactions are prone to oligomerization and formation of inflammatory aggregates due to low affinity thereof. The PYD interface match between $NLRP3^{PYD}$ and $ASC^{PYD}$ responsible for self-association and formation of the oligomeric $ASC^{PYD}$-$NLRP3^{PYD}$ heteromolecular complex (confirmed by structure-guided mutagenesis) provides the basis for inflammasome molecular activation. In order to block this self-oligomerization and formation of the heteromolecular complex, the interface of PYD in NLRP3 and interacting residue in ASC was investigated. When $NLRP3^{PYD}$ is present in the complex with $ASC^{PYD}$, PYD participates in a combination of type I, II, and III interactions to maintain the helical conformation (FIGS. 1A-C, 2A and 2B). Thereamong, the most important type I interface includes electrostatic interactions between α2 helices (K23, M27, E30, D31), α4 helices (D50, H51), and α1 helices (S5, R7, C8) of $NLRP3^{PYD}$ (FIG. 1B), and important electrostatic interactions between α2 helices (K21, S29, K26), al helices (R3, D6), and α4 helices (D48, D51) of $ASC^{PYD}$ (FIG. 1C). Nonetheless, the interaction varies as one promoter rotates relative to the other.

One scaffold of $ASC^{PYD}$ α2 helix and one scaffold of $NLRP3^{PYD}$ α2 helix were used to design the NIP (FIGS. 1A-C). Specifically, complementarity of the electrostatic surface was investigated to determine potential hotspots that could enhance the binding affinity between NIP and PYD. Mutations of suitable residues were implemented in all possible combinations, taking into account the accessible volume, electrostatic properties of the surface, binding energy and complex stability. The database of resulting peptides (258 mutations) with single substitutions and respective binding affinity and stability values thereof was recorded and used for the next round of residue scans.

In order to ensure the helicity of the designed peptide, a helical wheel plot (FIG. 3) was generated for the designed NIP and compared with the sequence of the helical region of the interacting PYD. According to the plot, the formation of an amphiphilic helical structure similar to the α-helix of interacting PYD was suggested. Based on affinity and stability scores, seven peptides were selected and labeled as NIP1-NIP7 (Table 1). These peptides were fused with cell-penetrating peptides and evaluated as NIP candidates.

Example 3: In-Vitro Screening and Evaluation of Inhibitory Effect of NIP

Cytotoxicity of the peptides was evaluated by MTT assay. THP1-derived macrophages were treated with NIP at concentrations of 1-50 μM. Cell viability assays showed that peptides except NIP2 and NIP4-6 were cytotoxic at 50 μM (FIG. 1D). Based on these results, it was assumed that treatment concentrations of up to 20 μM were safe, and additional experiments were conducted within the range of 1 to 20 μM.

Overall, activation of the NLRP3 inflammasome results not only in cleavage of pro-IL-1β and pro-IL-18, but also in release of active IL-1β and IL-18 and other soluble inflammatory mediators. Thus, NIP was mainly evaluated for regulatory effect on the NLPR3-mediated pathway through the assessment of IL-1β secretion. THP1-derived macrophages were primed with LPS (10 ng/ml) for 3 hours and then treated with peptides at different concentrations for 1 hour. Thereafter, the cells were cultured with nigericin (10 μM) for 2 hours, and the supernatant was collected to evaluate IL-1β secretion. Thereby, NIP3 was confirmed to most strongly inhibit NLPR3-mediated IL-1β secretion in a dose-dependent manner (FIG. 1E). In order to evaluate the $IC_{50}$ for NIP3, the peptide was tested three times at concentrations ranging from 1 nM to 20 μM, resulting in $IC_{50}$ values of 2.1-2.3 μM (FIG. 4A). Next, the regulatory effect of the peptide on the NLPR3 pathway was confirmed by evaluating IL-18 secretion and evaluating the expression levels of NLPR3-signaling downstream proteins. As expected, treatment of the cells with NIP3 significantly and dose-dependently reduced the amount of IL-18 secreted (FIG. 4B). Downstream-protein expression was also confirmed, and Western blotting showed that treatment of the cells with NIP3 significantly reduced the expression of NLPR3 and cleavage and activation of caspase-1 and IL-1β compared to untreated cells (FIG. 4C).

Example 4: Inhibition of NLRP3-Mediated Cytokine Production

Inflammasome formation requires coordinated priming and activation. Priming upregulates pattern recognition receptors such as TLR or NOD2 (nucleotide-binding oligomerization domain-containing protein 2) or acts through cytokines such as TNF-α and IL-1β that induce gene transcription after nuclear factor κB (NF-κB) activation and recognition of pathogen-associated or damage-associated molecular patterns (L. Franchi, et al., *J. Immunol.* 183, 792-796 (2009)). Activation signals provided by these patterns, including LPS, initiate various upstream signaling events, including potassium ($K^+$) or chloride ($Cl^-$) ion efflux, calcium ($Ca^{2+}$) flux, lysosomal disruption, and mitochondrial dysfunction to generate reactive oxygen species and trigger NLRP3 activation. Inflammasome formation activates caspase-1, which in turn cleaves pro-IL-1β and pro-IL-18. NLRP3 triggering by LPS requires a series of cellular events different from canonical activation.

Figure 4D:
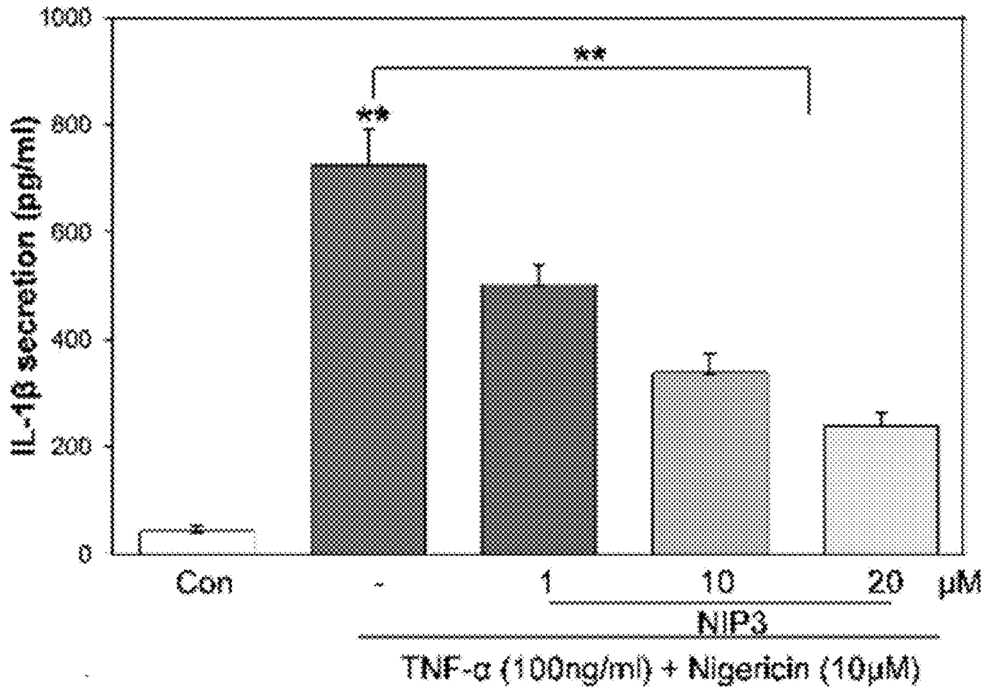
Figure 4E:
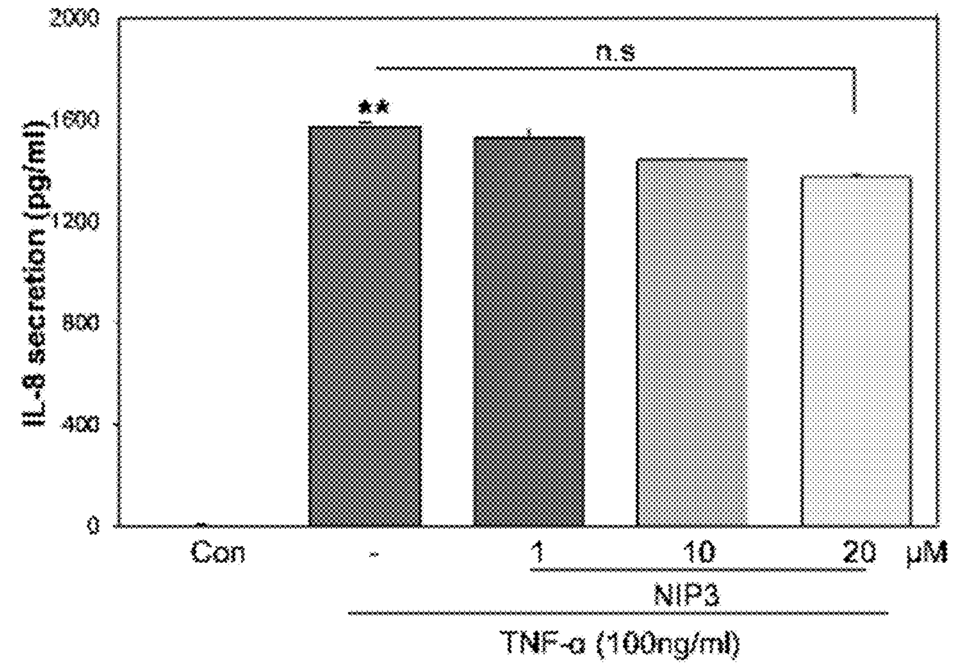
Figure 4F:
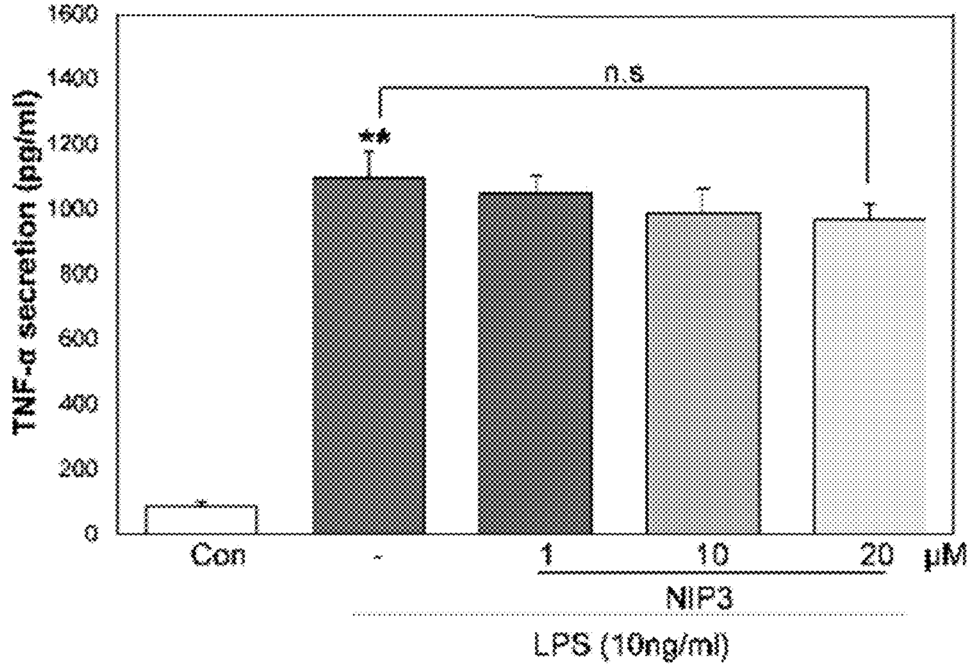

After identifying NIP3 as a potent inhibitor of NLRP3-mediated cytokine release and caspase-1 and IL-1β protein expression, the effects of NIP3 on the NLRP3 inflammasome-proximal pathway were investigated. Cells were primed with TNF-α to exclude the potential effect of LPS as an NLRP3-independent stimulus. The data suggest a strong inhibitory effect of NIP3 on the NLRP3 pathway regardless of the priming signal used (FIG. 4D). In addition, the influence of NIP3 on TNF-α secretion and TLR4-mediated signaling pathway was evaluated by analyzing the secretion levels of IL-8 and TNF-α. Thereby, the secretion of the two cytokines was not significantly delayed, indicating the specificity of the new inhibitor for NLRP3-mediated downstream signaling (FIGS. 4E and 4F).

Example 5: Affinity of NIP for NLRP3$^{PYD}$ and ASC$^{PYD}$

In order to confirm the binding mechanism of the peptide, umbrella sampling simulation was performed to determine PMF (potential mean force), which is helpful in determining ΔG for binding. Most of the binding energy values calculated from the PMF through umbrella sampling simulation are in close agreement with the experimental data (W. You, et sl., *J. Chem. Theory Comput.* 15, 2433-2443 (2019)). PMF curves were obtained for individual complexes using 14 sampling windows along the reaction coordinate axis (FIG. 5), and Δ for NIP1-ASC$^{PYD}$ binding and NIP3-NLRP3$^{PYD}$/ASC$^{PYD}$ binding was obtained (Table 3).

TABLE 3

Binding free energies for NIP1 and NIP3

| NIPs-PYD | $\Delta G_{Bind}$(kcal mol$^{-1}$) | $\Delta\Delta G_{Bind}$ (kcal mol$^{-1}$) |
|---|---|---|
| NIP1-ASC$^{PYD}$ | −7.4 | — |
| NIP3-ASC$^{PYD}$ | −8.8 | −1.4 |
| NIP3-NLRP3$^{PYD}$ | −6.8 | +0.6 |

Energy minima for NIP1-ASC$^{PYD}$, NIP3-ASC$^{PYD}$, and NIP3-NLRP3$^{PYD}$ occurred at center-of-mass (COM) distances of 0.47-0.5 nm in respective PMF curves thereof. For NIP3, the minimum energy was found to be at about 0.47 nm because NIP3 is in close contact with ASC$^{PYD}$. The A of binding to NIP1 is-7.4 kcal mol$^{-1}$, whereas the binding affinities of NIP3 to ASC$^{PYD}$ and NLRP3$^{PYD}$ are −8.8 and −6.8 kcal mol$^{-1}$, respectively. NIP3 forms a strong bond with PYD due to the large electrostatic charge difference between the interacting residues. The A values calculated from the experimentally determined $K_d$ values of LRP3$^{PYD}$-ASC$^{PYD}$ and ASC$^{PYD}$-ASC$^{PYD}$ (J. Oroz, et al., *J. Biol. Chem.* 291, 19487-19501 (2016)) fell in the range of −2.463 to −2.717 kcal mol$^{-1}$. The binding energy suggests that the peptide has the potential to disrupt the NLRP3$^{PYD}$-ASC$^{PYD}$ interaction and ASC$^{PYD}$-ASC$^{PYD}$ self-association.

INDUSTRIAL APPLICABILITY

According to the present invention, abnormal intrinsic dysregulation of the NLRP3 inflammasome system has been implicated in the pathogenesis of a large number of infectious and autoimmune diseases. In the present invention, peptides that block NLRP3 signaling were identified, and the α2-helix-derived peptide NIP3, which targets only ASC$^{PYD}$ and NLRP3$^{PYD}$, was proved to be effective in vitro and to significantly inhibit the production of IL-1β and IL-18 mediated by the NLRP3 pathway. Therefore, NIP3 is regarded as an effective therapeutic agent for NLRP3 inflammasome-related diseases.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

Sequence List Free Text

An electronic file is attached.

The invention claimed is:

1. A peptide consisting of the amino acid sequence of SEQ ID NO: 3.

2. The peptide according to claim 1, wherein the peptide downregulates interleukin 1β (IL-1β) and interleukin 18 (IL-18) by inhibiting NLRP3 inflammasome signaling.

3. A fusion peptide in which the peptide according to claim 1 and a cell-penetrating peptide (CPP) are conjugated.

4. A composition comprising the peptide according to claim 1 or a fusion peptide comprising the peptide and a cell-penetrating peptide (CPP) conjugated thereto.

5. A method for inhibiting NLRP3 inflammasome activity or treating an NLRP3 inflammasome-related inflammatory disease in a subject in need thereof, comprising administering to the subject an effective amount of the peptide according to claim 1 or a fusion peptide comprising the peptide and a cell-penetrating peptide (CPP) conjugated thereto.

6. The method according to claim 5, wherein the NLRP3 inflammasome-related inflammatory disease is a metabolic disease, a neuroinflammatory disease, or an autoinflammatory disease.

7. The method according to claim 6, wherein the metabolic disease is obesity, hyperlipidemia, hypercholesterolemia, arteriosclerosis, type 2 diabetes mellitus, nonalcoholic fatty liver disease (NAFLD), or nonalcoholic steatohepatitis (NASH).

8. The method according to claim 6, wherein the neuroinflammatory disease is Alzheimer's disease, gout, Parkinson's disease, Huntington's disease, Lou Gehrig's disease, Creutzfeldt-Jakob disease, multiple sclerosis, amyotrophic lateral sclerosis, diffuse Lewy body disease, leukoencephalitis, temporal lobe epilepsy, or inflammatory spinal cord injury.

9. The method according to claim 6, wherein the autoinflammatory disease is Muckle-Wells syndrome (MWS), latent autoimmune diabetes in adults (LADA), familial cold autoinflammatory syndrome (FCAS), cryopyrin-associated periodic syndrome (CAPS), neonatal-onset multisystem inflammatory disease (NOMID), chronic infantile neurologic cutaneous and articular (CINCA) syndrome, familial Mediterranean fever (FMF), systemic juvenile idiopathic arthritis (SJIA), systemic juvenile idiopathic rheumatoid arthritis, or rheumatoid arthritis.

10. The composition according to claim 4, which is a pharmaceutical composition or a food composition.

* * * * *